United States Patent
Mandakolathur Vasudevan et al.

(10) Patent No.: US 9,549,738 B2
(45) Date of Patent: Jan. 24, 2017

(54) RATCHETING FEATURE ON TISSUE STAPLE TRIGGER TO PREVENT PREMATURE JAW OPENING

(75) Inventors: Venkataramanan Mandakolathur Vasudevan, Cincinnati, OH (US); Adam R. Dunki-Jacobs, Cincinnati, OH (US); Chester O. Baxter, III, Loveland, OH (US); Jerome R. Morgan, Cincinnati, OH (US); Cortney E. Henderson, Loveland, OH (US); Christopher C. Miller, Loveland, OH (US); Kent P. Baker, Liberty Township, OH (US); John V. Hunt, Cincinnati, OH (US); Barry T. Jamison, Fairfield, OH (US); Patrick A. Weizman, Liberty Township, OH (US); Joseph E. Young, Loveland, OH (US); Cory G. Kimball, Cincinnati, OH (US); Carl J. Shurtleff, Mason, OH (US); Edward G. Chekan, Cincinnati, OH (US); Kevin D. Felder, Cincinnati, OH (US); Johnny H. Alexander, III, West Chester, OH (US); Patrick J. Swindon, Cincinnati, OH (US); Joseph P. Schowalter, South Lebanon, OH (US); John F. Cummings, Madeira, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1190 days.

(21) Appl. No.: 13/344,093

(22) Filed: Jan. 5, 2012

(65) Prior Publication Data
US 2013/0175320 A1     Jul. 11, 2013

(51) Int. Cl.
*A61B 17/00* (2006.01)
*A61B 17/115* (2006.01)
(Continued)

(52) U.S. Cl.
CPC ......... *A61B 17/1155* (2013.01); *A61B 17/072* (2013.01); *A61B 2017/00407* (2013.01); *A61B 2017/2923* (2013.01)

(58) Field of Classification Search
CPC .................. A61B 17/068; A61B 2017/00407; A61B 2017/2923
(Continued)

(56) References Cited

U.S. PATENT DOCUMENTS

| 4,805,823 A | 2/1989 | Rothfuss |
| 5,205,459 A | 4/1993 | Brinkerhoff et al. |

(Continued)

FOREIGN PATENT DOCUMENTS

| EP | 0 589 306 | 3/1994 |
| EP | 0 760 230 | 3/1997 |

(Continued)

OTHER PUBLICATIONS

International Search Report dated Mar. 22, 2013 for Application No. PCT/US2012/069998.
(Continued)

*Primary Examiner* — Andrew M Tecco
*Assistant Examiner* — Chelsea Stinson
(74) *Attorney, Agent, or Firm* — Frost Brown Todd LLC

(57) ABSTRACT

A surgical instrument includes a body, a pivotable trigger, and a ratcheting assembly. The ratcheting assembly may include a rotary ratchet coupled to the trigger and a pawl coupled to the body. The rotary ratchet may further include a ramp that disengages the ratchet from the pawl. A release feature may be included to selectively disengage a second (Continued)

member of the ratcheting assembly from a first member. In some versions, the release feature may include a rotation knob or a slidable handle. In another configuration, the ratcheting assembly may have a first member coupled to an actuator and a second member coupled to the body. The assembly may include a lock member coupled to the body that selectively engages a plurality of teeth disposed on the actuator. Alternatively, the assembly may include a pivotable pawl coupled to the actuator that engages one or more notches formed in the body.

8 Claims, 19 Drawing Sheets

(51) Int. Cl.
　　*A61B 17/072* (2006.01)
　　*A61B 17/29* (2006.01)
(58) Field of Classification Search
　　USPC .................... 227/175.1–182.1, 901, 902
　　See application file for complete search history.

(56) References Cited

U.S. PATENT DOCUMENTS

| | | | |
|---|---|---|---|
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,415,334 A | 5/1995 | Williamson, IV et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,783,524 B2 | 8/2004 | Anderson et al. | |
| 6,817,508 B1 * | 11/2004 | Racenet | A61B 17/068 227/175.2 |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,275,674 B2 * | 10/2007 | Racenet | A61B 17/068 227/175.1 |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,020,743 B2 * | 9/2011 | Shelton, IV | A61B 17/07207 227/175.1 |
| 8,083,120 B2 * | 12/2011 | Shelton, IV | A61B 17/07207 227/175.1 |
| 8,136,711 B2 | 3/2012 | Beardsley et al. | |
| 2006/0000867 A1 * | 1/2006 | Shelton | A61B 17/07207 227/175.1 |
| 2008/0167672 A1 * | 7/2008 | Giordano | A61B 17/07207 606/167 |
| 2008/0314955 A1 * | 12/2008 | Boudreaux et al. | 227/175.2 |
| 2008/0314958 A1 * | 12/2008 | Scirica | A61B 17/07207 227/175.2 |
| 2009/0206124 A1 * | 8/2009 | Hall et al. | 227/175.1 |
| 2010/0065605 A1 * | 3/2010 | Shelton, VI | A61B 17/07207 227/176.1 |
| 2014/0367448 A1 * | 12/2014 | Cappola | A61B 17/29 227/177.1 |

FOREIGN PATENT DOCUMENTS

| | | |
|---|---|---|
| EP | 2 000 102 | 12/2008 |
| WO | WO 2008/002417 | 1/2008 |
| WO | WO 2010/108213 | 9/2010 |

OTHER PUBLICATIONS

Chinese Office Action dated Jan. 18, 2016 for Application No. 201280066087.1, 10 pages.
Chinese Search Report dated Dec. 24, 2015 for Application No. 201280066087.1, 3 pages.
International Preliminary Report on Patentability dated Jul. 8, 2014 for Application No. PCT/US2012/069998, 8 pages.

* cited by examiner

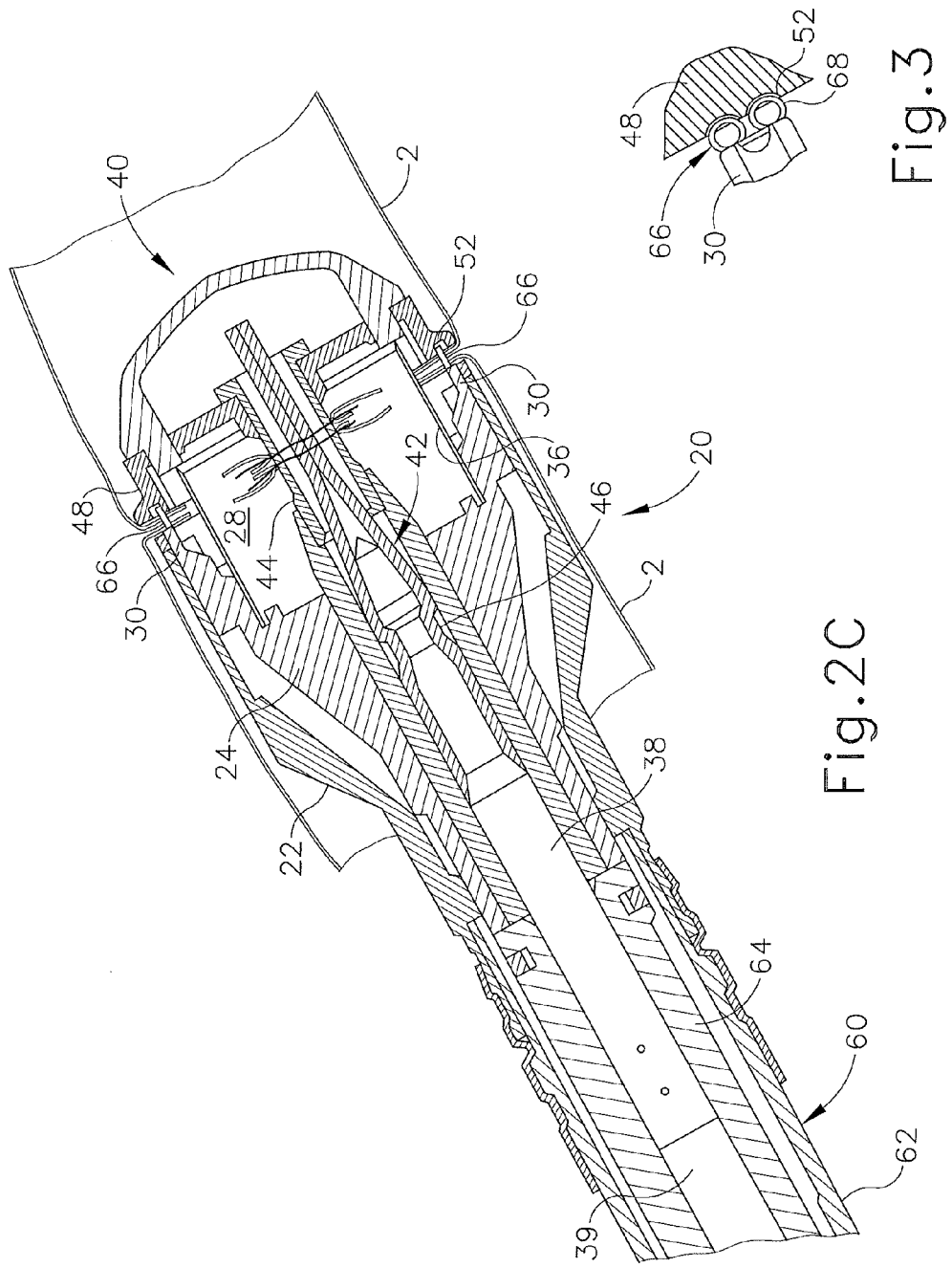

RATCHETING FEATURE ON TISSUE STAPLE TRIGGER TO PREVENT PREMATURE JAW OPENING

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions will need to be recoupled together. One such tool for accomplishing these anastomotic procedures is a circular stapler that is inserted through a patient's orifice.

Examples of such circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

Figure 6:
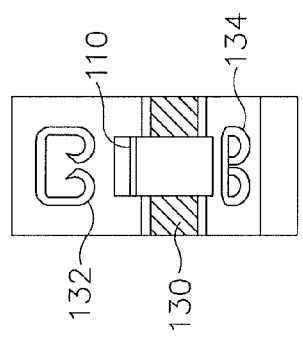
FIG. 6 depicts an diagrammatic view of the indicator window of FIG. 5 showing an exemplary indicator bar and exemplary corresponding staple representations.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 1:
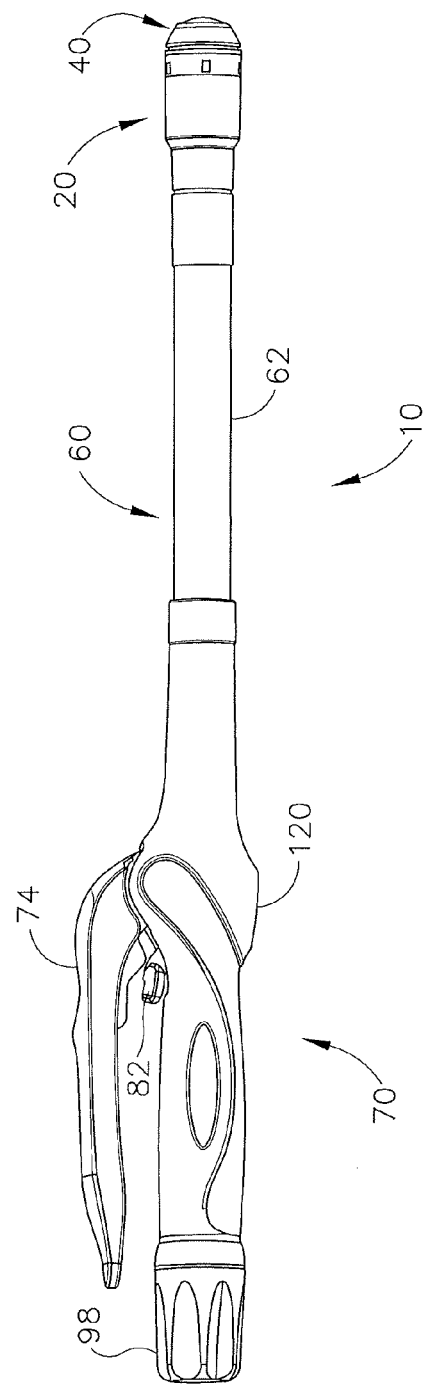
FIG. 1 depicts a side elevation view of an exemplary circular stapling surgical instrument.
Figure 2A:
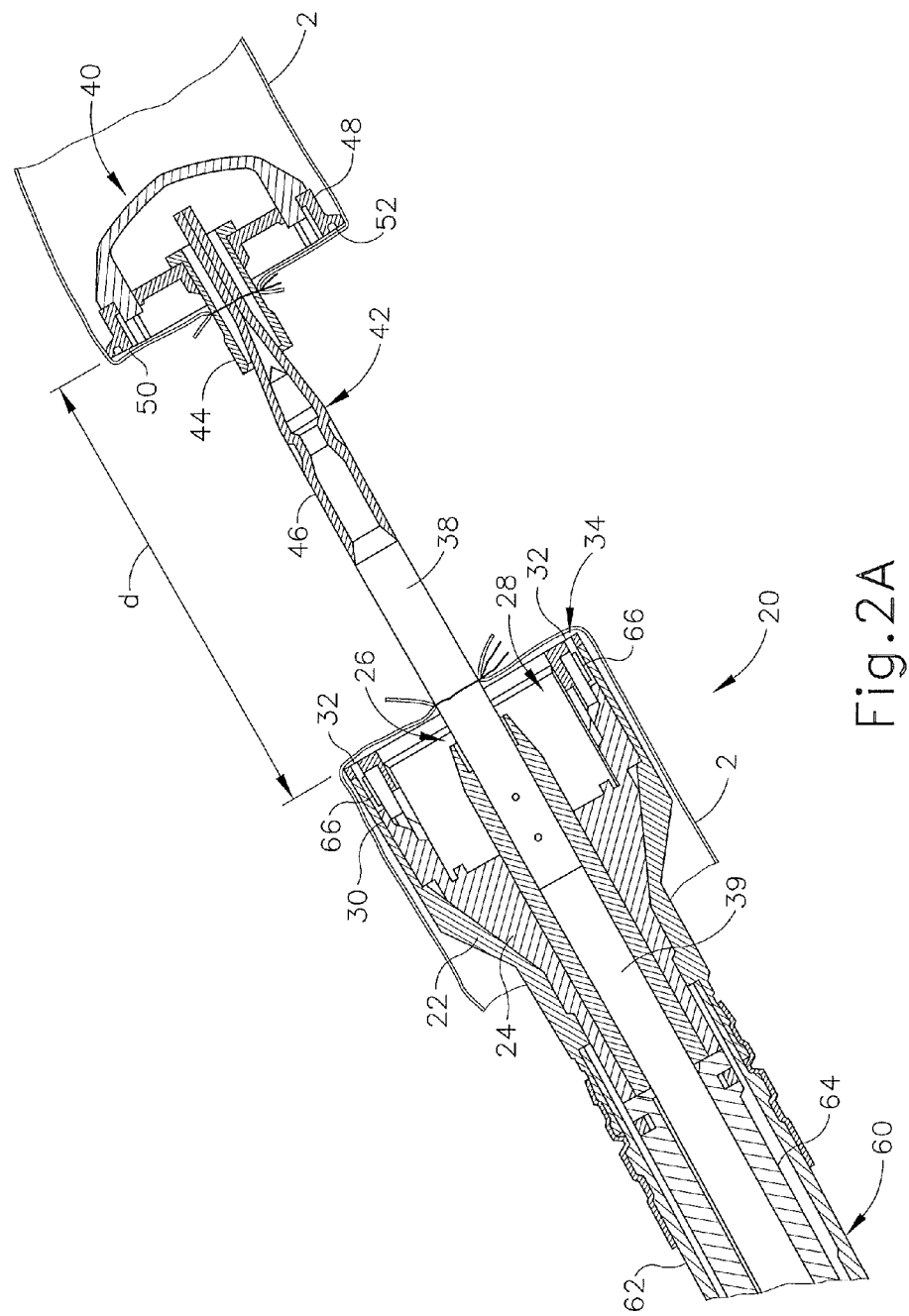
FIG. 2A depicts an enlarged longitudinal cross-section view of an exemplary stapling head assembly of the instrument of FIG. 1 showing an exemplary anvil in an open position.
Figure 2B:
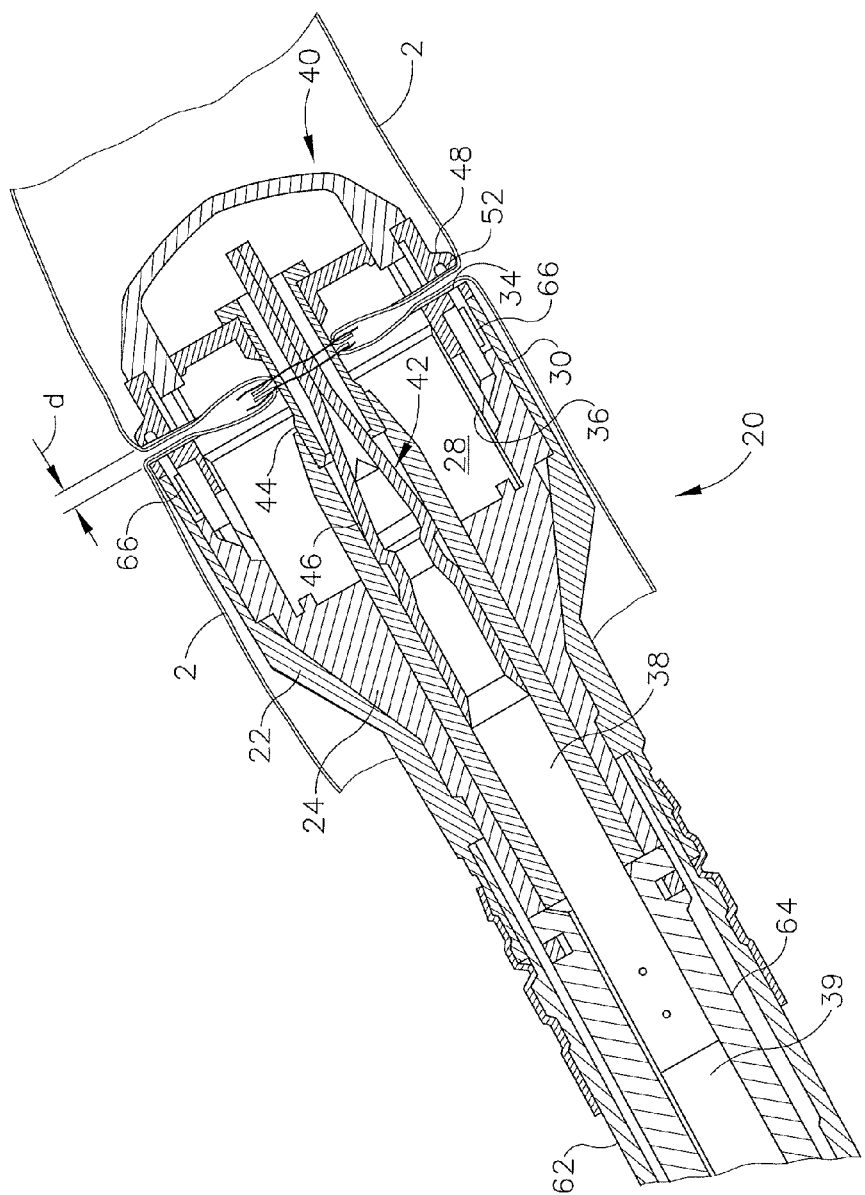
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples. It should be understood that staple forming pockets (52) are merely optional and may be omitted in some versions.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
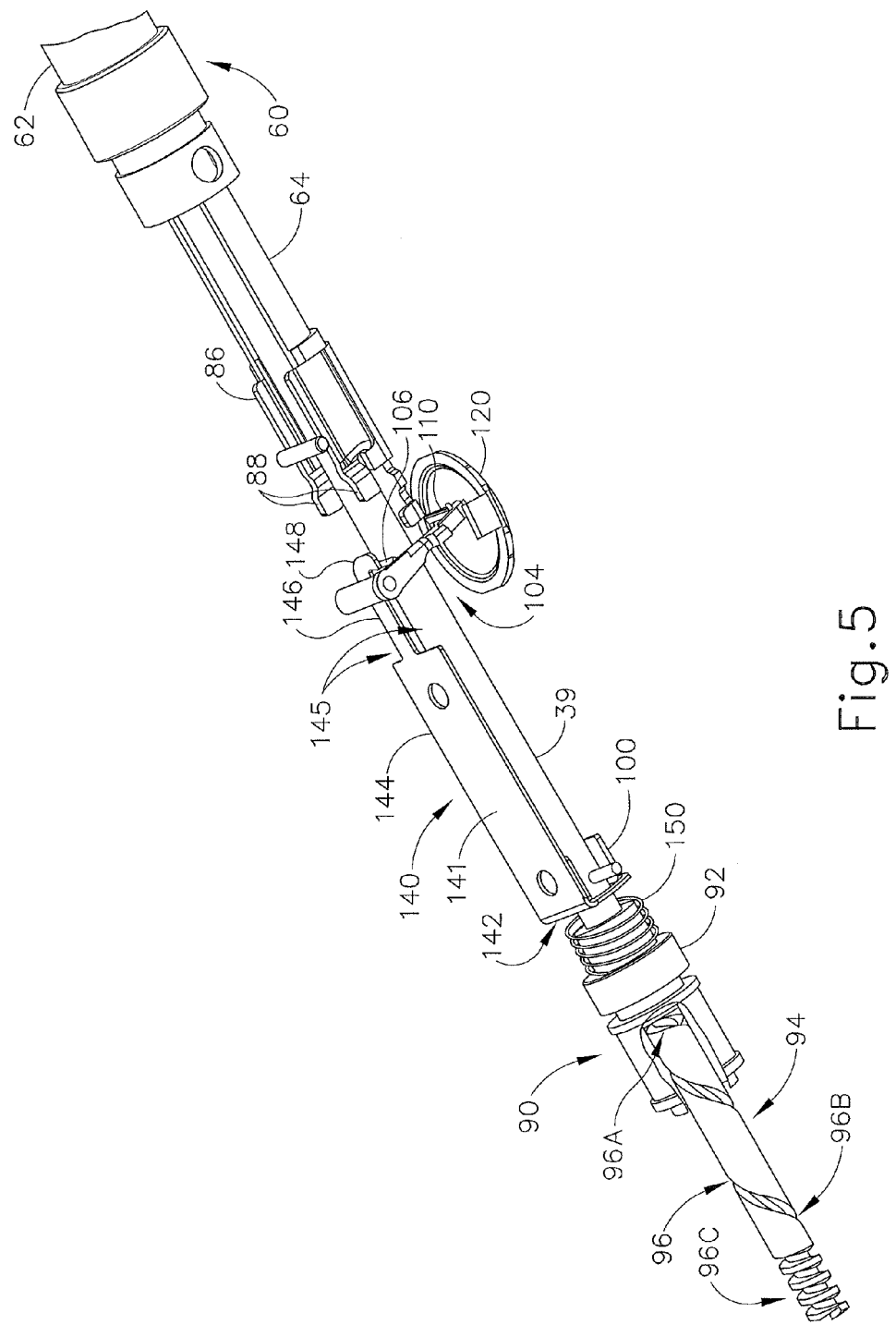
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
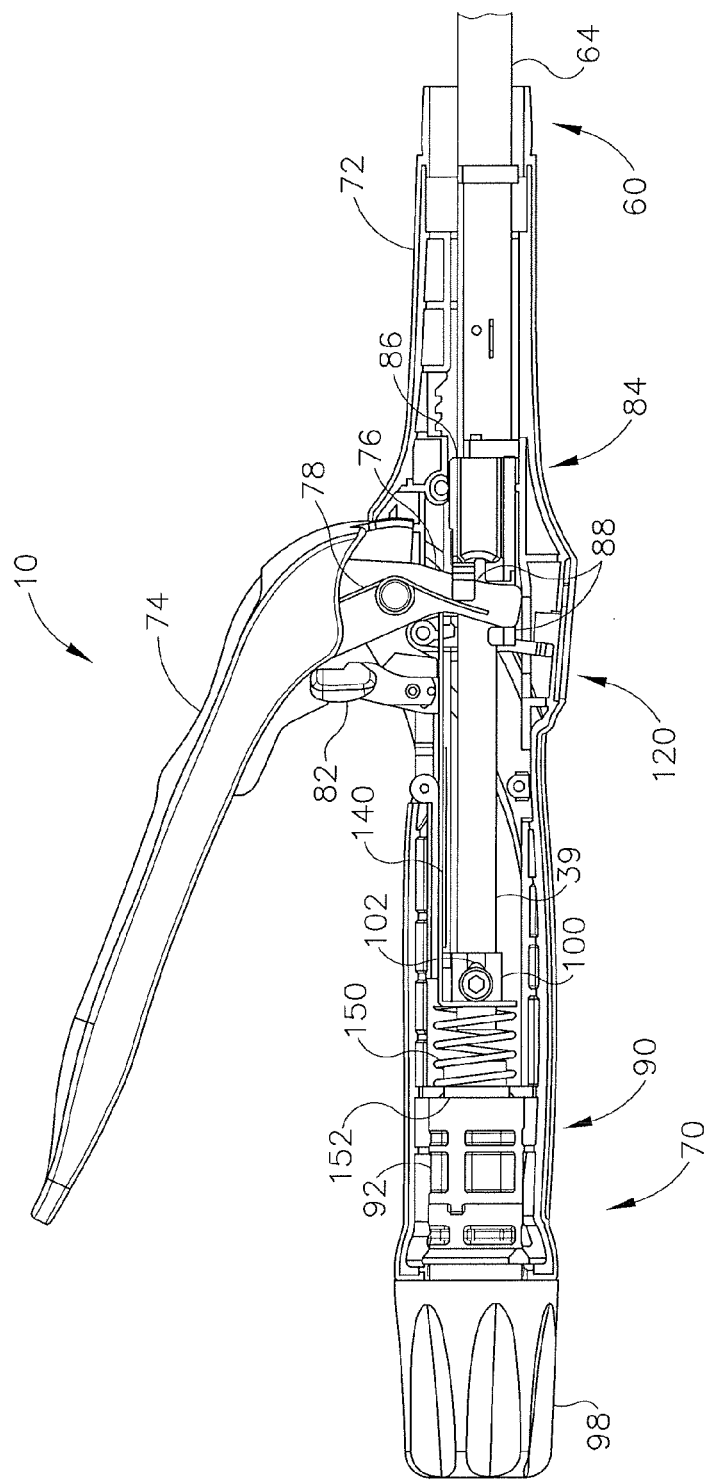
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
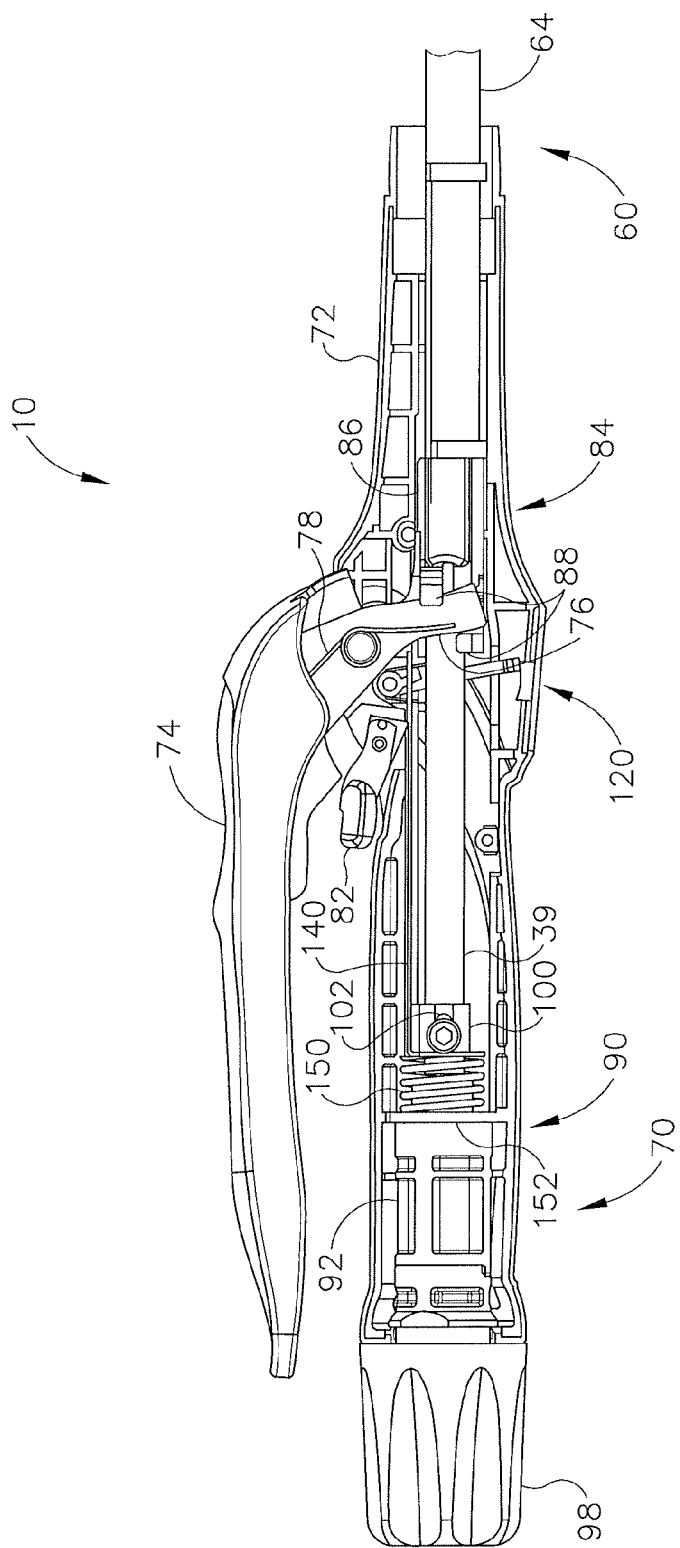
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). U-shaped clip (100) engages with a portion of body (72) to substantially prevent trocar actuator (39) from rotating about its axis when adjusting knob (98) is rotated. U-shaped clip (100) further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

II. Exemplary Trigger Ratcheting Features

In some instances, it may be preferable to prevent trigger (74) from pivoting back to an unfired position when trigger (74) is only partially actuated. For instance, if trigger (74) is initially pivoted, staples (66) may be driven out of stapling head assembly (20), but have yet to enter staple forming pockets (52). Accordingly, staples (66) may be partially embedded in tissue (2), but legs (68) may still be jutting out of tissue (2) when trigger (74) is still in the middle of a firing stroke. If trigger (74) is prematurely released, thereby retracting staple driver (24), then staples (66) may remain embedded in tissue (2) in an unformed configuration and will not have stapled together tissue (2). In addition, if the user attempts to fire the device again, staples (66) may have misaligned such that staple driver (24) does not fully engage staples (66) and/or such that staples (66) are no longer aligned with staple forming pockets (52). This may result in malformed staples (66), incompletely bent staples (66), etc. Moreover, with knife (36) actuated as well, knife (36) may sever a portion of tissue (2) that was not intended to be severed. Accordingly, various ratcheting features may be used with trigger (74) such that trigger (74) is prevented from returning to the unfired position until trigger (74) completes a full firing stroke. In some versions, it may be useful to also include a release feature to disengage the ratcheting mechanism prior to full engagement. Such release features may be used to abort the stapling procedure if the need arises.

A. Exemplary Rotary Ratcheting Assembly

Figure 7:
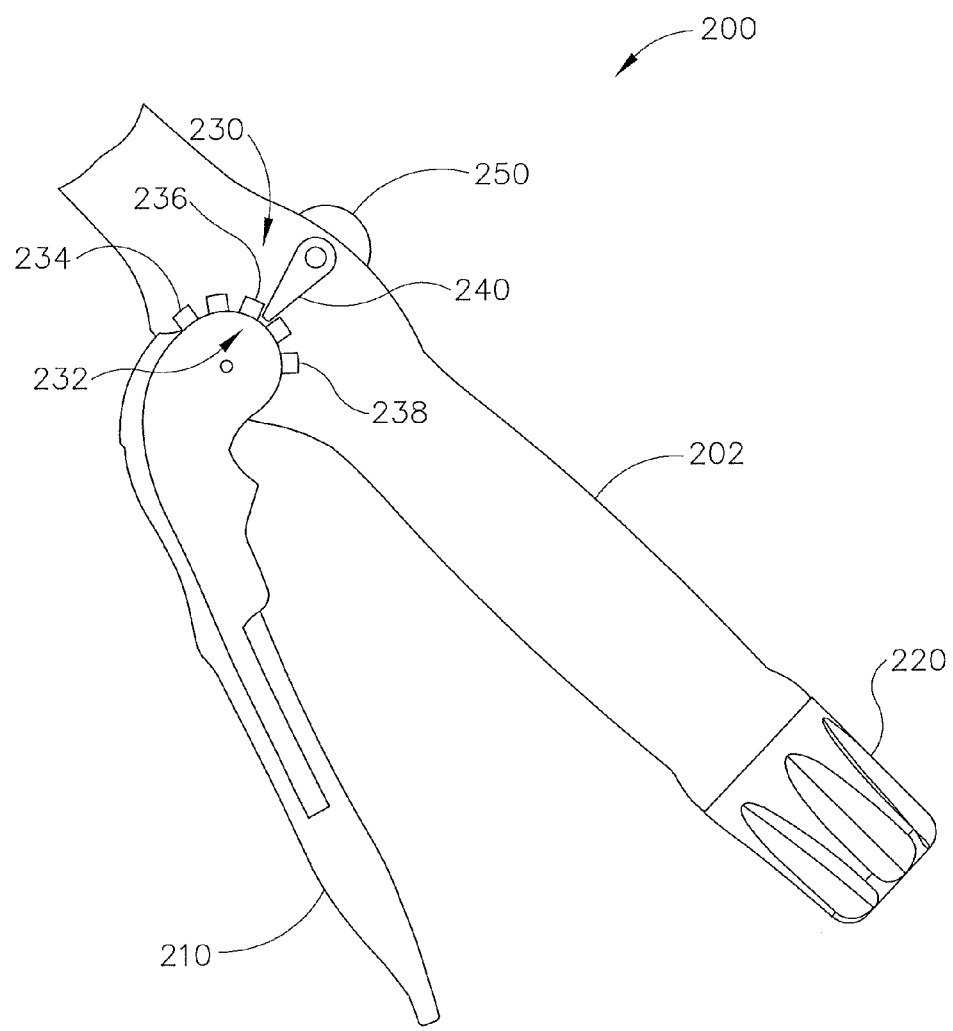
FIG. 7 depicts a side elevation view of an exemplary actuator handle assembly with a portion of the body removed to show an exemplary rotary ratcheting assembly.

FIG. 7 depicts one exemplary alternative actuator handle assembly (200) for surgical stapling instrument (10) described above. In the present example, actuator handle assembly (200) comprises a body (202), a trigger (210), and an adjusting knob (220). Body (202), trigger (210), adjusting knob (220), and/or actuator handle assembly (200) may be constructed in accordance with at least some of the teachings of body (72), trigger (74), adjusting knob (98), and/or actuator handle assembly (70) described above. Trigger (210) of the present example is pivotably mounted to body (202) and is coupled to a rotary ratcheting assembly (230). Trigger (210) of the present example further includes a return spring (not shown) operable to urge trigger (210) back to the unfired position, though this is merely optional. Rotary ratcheting assembly (230) comprises a plurality of teeth (232) and a pawl (240). Teeth (232) are disposed about a pivotable end (212) of trigger (210) and include an initial tooth (234) and a final tooth (238).

Initial tooth (234) may be engaged with pawl (240) when trigger (210) is in the initial, unfired position, though this is merely optional. In some versions, initial tooth (234) may be disposed on pivotable end (212) such that pawl (240) does not engage initial tooth (234) until trigger (210) is pivoted a predetermined distance. For instance, such an assembly may be configured such that initial tooth (234) only engages pawl (240) once trigger (210) has actuated a staple driver and staples to a predetermined point. By way of example only, such a predetermined point may be when the staples, such as staples (66), protrude out of a distal end of a stapling head assembly, such as stapling head assembly (20). Alternatively, such a predetermined point may be after the staples protrude out of the stapling head assembly and pierce tissue, after staples begin to engage a plurality of staple forming pockets, or at any point after the staples begin to exit the stapling head assembly. In another version, the predetermined point may be before the staples protrude from stapling head assembly. Still further positioning and configurations for initial tooth (234) will be apparent to one of ordinary skill in the art in view of the teachings herein.

The plurality of teeth (232) terminate at a final tooth (238) positioned at a circumferential point on pivotable end (212) that is different than initial tooth (234). As trigger (210) is pivoted toward the fired position, such as that shown in FIG. 4, pawl (240) successively engages the interposed teeth (232) until final tooth (238). Final tooth (238) may correspond to when trigger (210) is in the fired position or, alternatively, final tooth (238) may be positioned at any other corresponding position. In the first instance, if trigger (210) is released before trigger (210) is fully actuated, teeth (232) engage pawl (240), described below, and prevent trigger (210) from returning to the unfired position. Trigger (210) may then be re-grasped and complete firing may be performed. Final tooth (238) maintains trigger (210) in the fired position until release knob (250), described below, is rotated to disengage pawl (240). In versions without release knob (250), final tooth (238) maintains trigger (210) in the fired position even when trigger (210) is released after a complete firing. The user may then remove the surgical instrument, leaving behind the stapled tubular tissue (2).

In the second instance noted above, final tooth (238) may not coincide with the fired position of trigger (210). For instance, final tooth (238) may be positioned at a point where the staples begin to engage the staple forming pockets. Accordingly, if trigger (210) is released at this point, staples have begun to enter staple forming pockets and the staple driver may remain engaged with the staples. The user may then finish pivoting trigger (210) to completely form the staples. Such a position for final tooth (238) may be advantageous if repeated actuation of trigger (210) is necessary to cleave any excess tissue (2). Of course other, intermediate positions for final tooth (238) will be apparent to one of ordinary skill in the art in view of the teachings herein.

In yet a further alternative, final tooth (238) may be spaced apart from a terminal intermediate tooth (236). For instance, terminal intermediate tooth (236) may be positioned in accordance with a point where the staples begin to engage the staple forming pockets, such as that described above. Accordingly, if repeated actuation of trigger (210) is required, ratcheting assembly (230) may catch on terminal intermediate tooth (236) to prevent trigger (210) from returning to the unfired position. Final tooth (238) secures trigger (210) in the final position to prevent trigger (210) from actuating back to the unfired position.

The gap described above between terminal intermediate tooth (236) and final tooth (238) may also be used to provide audible, tactile, visual, and/or other sensory feedback to a user regarding the position of trigger (210) relative to the firing of the staple driver. By way of example only, teeth (232) may be configured to provide an audible and tactile "click" when engaging pawl (240). In addition, or in the alternative, electrical contacts may be positioned on teeth (232) to engage a complementary electrical contact on pawl (240). For instance, initial tooth (234) may light up a green LED to indicate initial engagement of trigger (210), the interposed teeth (232) before final tooth (238) may light up a yellow LED indicating incomplete firing, and engagement of final tooth (238) may light up a red LED indicating completed firing. Of course it should be understood that other configurations and uses for ratcheting assembly (230) will be apparent to one of ordinary skill in the art.

Pawl (240) of the present example comprises a spring-loaded camming tooth that engages teeth (232) to prevent trigger (210) from pivoting back to the unfired position. In the present example, pawl (240) is coupled to a release knob (250). Release knob (250) extends out of body (202) such that a user may rotate release knob (250) to disengage pawl (240) from teeth (232). Accordingly, if trigger (210) initially engages teeth (232), release knob (250) may be used to unlock trigger (210) to return to the unfired position. In addition, if trigger (210) has been fully fired and tissue (2) is snagged on the knife and/or any other portion of the stapling head assembly, release knob (250) may be used to release trigger (210) to free the surgical instrument from tissue (2). Still further constructions for pawl (240) and/or release knob (250) will be apparent to one of ordinary skill in the art in view of the teachings herein. For example, release knob (250) could comprise a slider with an integral rack that is coupled to pawl (240), a push button that is coupled with pawl (240) via a rack or linkage, and/or otherwise.

In some versions, rotary ratcheting assembly (230) may be configured as a linear ratcheting assembly. For instance, trigger (210) may engage and actuate a rack gear, such as rack gear (714) described below in reference to FIGS. 14A-14C. Pawl (240) then engages the rack gear in a similar manner to teeth (232) of rotary ratcheting assembly (230). Furthermore, it should be understood that pawl (240) may be disposed within or against the trigger (210), and teeth (232) may be disposed within or against the body (202), such that rotation of trigger (210) causes a rotation of pawl (240) and engagement of teeth (234, 236, 238). Of course the foregoing configurations are merely exemplary and alternative ratcheting assemblies will be apparent to one of ordinary skill in the art in view of the teachings herein.

B. Alternative Ratcheting Assembly

Figure 8:
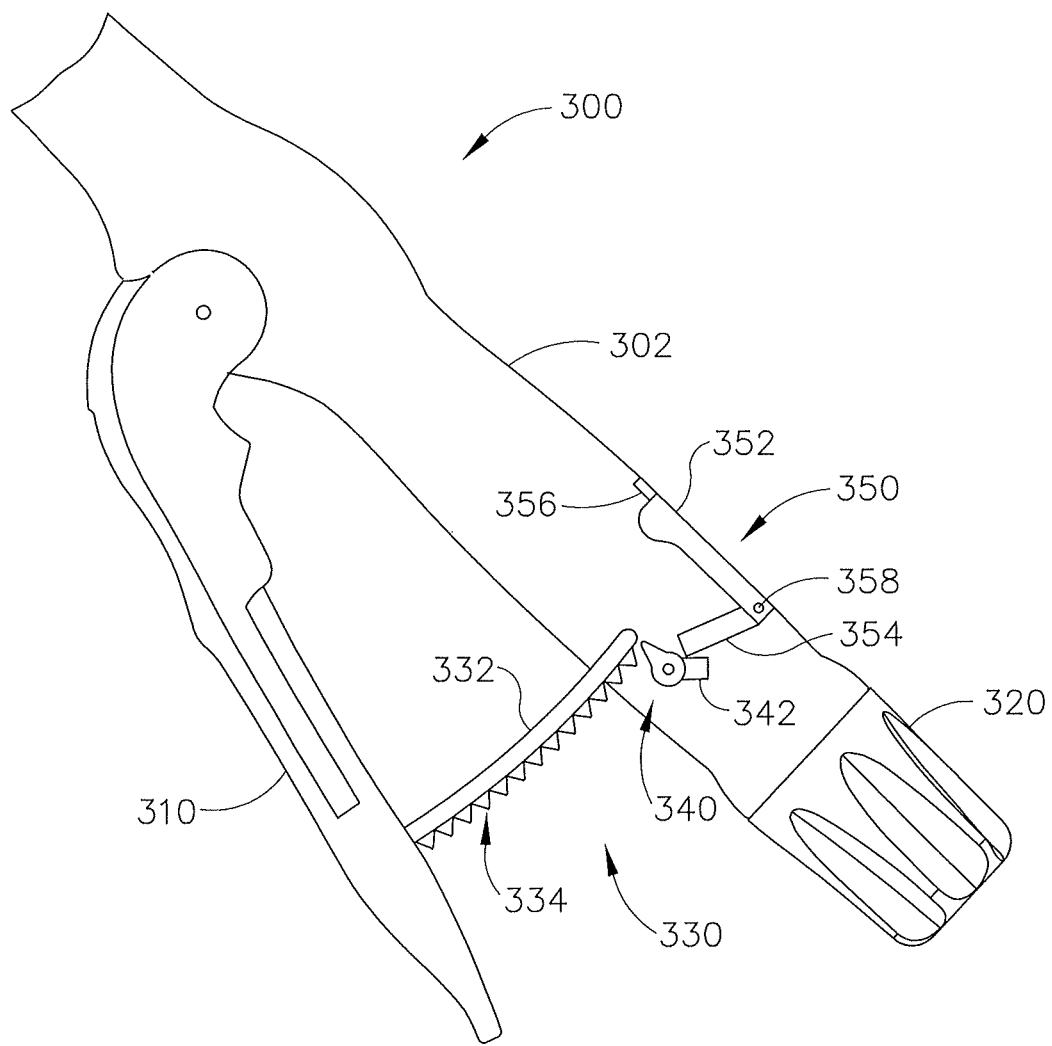
FIG. 8 depicts a side elevation view of an exemplary alternative actuator handle assembly with a portion of the body removed to show an exemplary alternative ratcheting assembly.

FIG. 8 depicts an alternative actuator handle assembly (300) having an exemplary alternative ratcheting assembly (330) for surgical stapling instrument (10) described above. In the present example, actuator handle assembly (300) comprises a body (302), a trigger (310), and an adjusting knob (320). Body (302), trigger (310), adjusting knob (320), and/or actuator handle assembly (300) may be constructed in accordance with at least some of the teachings of body (72), trigger (74), adjusting knob (98), and/or actuator handle assembly (70) described above. Trigger (310) of the present example is pivotably mounted to body (302) and is coupled to an arcuate member (332) having a plurality of teeth (334). In some versions, trigger (310) may include a return spring (not shown) operable to urge trigger (310) back to the unfired position.

Ratcheting assembly (330) comprises arcuate member (332) and a pawl (340) that engages and prevents trigger (310) from pivoting back to an unfired position. By way of example only, ratcheting assembly (330) may be configured similarly to the ratcheting assembly of handcuffs and/or a zip tie. Arcuate member (332) is curved such that each successive tooth of teeth (334) engages pawl (340). Accordingly, as trigger (310) is pivoted toward body (302), teeth (334) engage pawl (340) and sequentially lock trigger (310) from actuating back to the unfired position. Teeth (334) may be further constructed in accordance with at least some of the teachings of teeth (232) described above.

Pawl (340) of the present example comprises a spring-loaded pivoting tooth that engages and locks teeth (334). A release tab (342) extends from pawl (340). When release tab (342) is rotated clockwise (relative to the view shown in FIG. 8), pawl (340) disengages teeth (334) such that trigger (310) may return to the unfired position. In the present example, a release assembly (350) is pivotably mounted to body (302) via pivot point (358) and includes an outer member (352) and an inner pivot member (354). In the present example, inner pivot member (354) is configured to abut release tab (342) on a distal side of release tab (342). Accordingly, as will be apparent to one of ordinary skill in the art in view of the teachings herein, when inner pivot member (354) is rotated counterclockwise (relative to the view shown in FIG. 8) about pivot point (358), inner pivot member (354) engages and rotates release tab (342) to disengage pawl (340) from teeth (334). Inner pivot member (354) is fixedly secured to outer member (352). Accordingly, when outer member (352) is depressed inwardly into body (302), outer member (352) rotates inner pivot member (354) about pivot point (358) to disengage pawl (340). Of course other arrangements for release assembly (350) will be apparent to one of ordinary skill in the art in view of the teachings herein.

In the example shown, outer member (352) includes a break-away tab (356) that secures outer member (352) relative to body (302). By way of example only, break-away tab (356) may extend distally and abut an exterior surface of body (302) and/or break-away tab (356) may be integrally formed with body (302). Breakaway tab (356) may comprise a plastic member that is configured to break when a sufficient force is applied to outer member (352). Accordingly, an outer member (352) may be prevented from being depressed inwardly relative to body (302) until break-away tab (356) is broken. Such a break-away tab (356) may prevent inadvertent releases of pawl (340). Of course other components to secure outer member (352) relative to body (302) will be apparent to one of ordinary skill in the art in view of the teachings herein. For example, spring-loaded locks, slide locks, screws, pins, clips, clamps, adhesives, etc may be used.

Further configurations for actuator handle assembly (300) and/or ratcheting assembly (330) will be apparent to one of ordinary skill in the art in view of the teachings herein.

C. Chevron Ratchet Assembly

Figure 10:
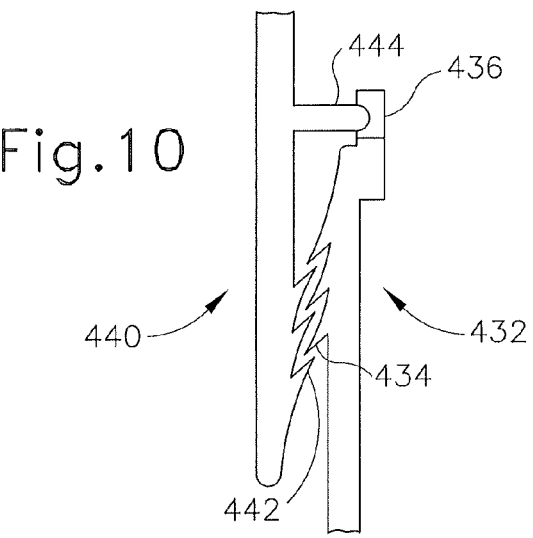
FIG. 10 depicts a partial side elevation view showing the two-piece ratchet assembly of FIG. 9 engaged together.
Figure 9:
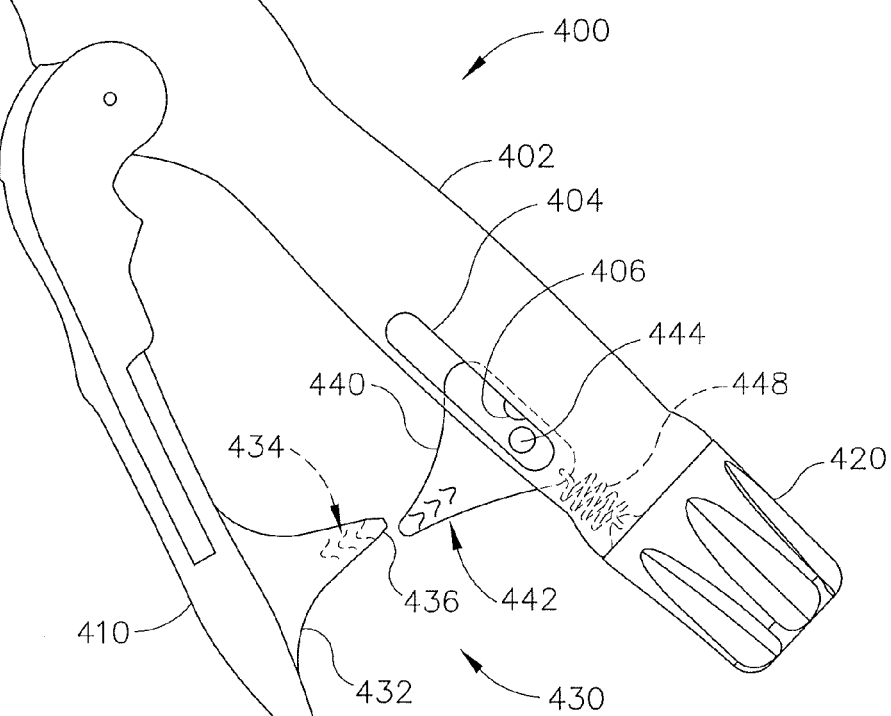
FIG. 9 depicts a side elevation view of yet another exemplary actuator handle assembly showing an exemplary chevron ratchet assembly.

FIGS. 9-10 depict an alternative actuator handle assembly (400) having an exemplary chevron ratchet assembly (430) for surgical stapling instrument (10) described above. In the present example, actuator handle assembly (400) comprises a body (402), a trigger (410), and an adjusting knob (420). Body (402), trigger (410), adjusting knob (420), and/or actuator handle assembly (400) may be constructed in accordance with at least some of the teachings of body (72), trigger (74), adjusting knob (98), and/or actuator handle assembly (70) described above. Trigger (410) of the present example is pivotably mounted to body (402) and is coupled to a first ratcheting member (432) having one or more chevron teeth (434). In some versions, trigger (410) may include a return spring (not shown) operable to urge trigger (410) back to the unfired position.

Chevron ratchet assembly (430) of the present example comprises a two-piece assembly with a first ratcheting member (432) fixedly mounted to trigger (410) and a second ratcheting member (440) longitudinally slidably mounted to body (402). First ratcheting member (432) comprises a one or more chevron teeth (434) configured to engage with one or more chevron teeth (442) on second ratcheting member (440) that complement chevron teeth (434). In the present example, chevron teeth (434, 442) comprise deformable or otherwise semi-malleable teeth such that an application of lateral force relative to the teeth (434, 442) can deform a portion of each tooth while an application of vertical force relative to the teeth (434, 442) does not deform the teeth (434, 442). Of course teeth (434, 442) may have other shapes, such as teeth (534) shown in FIG. 11 or any other shape as will be apparent to one of ordinary skill in the art in view of the teachings herein. Accordingly, as trigger (410) is pivoted to fire the instrument, teeth (434, 442) engage to prevent trigger (410) from returning to the unfired position.

Second ratcheting member (440) of the present example is slidably mounted to body (402) such that second ratcheting member (440) may be actuated longitudinally relative to body (402) and/or first ratcheting member (432). In the example shown, second ratcheting member (440) includes a peg (444) that rides within a slot (404) formed in body (402). Accordingly, if second ratcheting member (440) is engaged with first ratcheting member (432) and a user wants to release trigger (410), the user grasps peg (444) and slides second ratcheting member (440) distally relative to first ratcheting member (432). Accordingly, as shown in FIG. 10, teeth (442) of second ratcheting member (440) can slide longitudinally relative to teeth (434) of first ratcheting member (432) and/or partially deform teeth (434, 442) until teeth (434, 442) are clear of each other. The trigger (410) may then be actuated back to the unfired position or any intermediary position. Such actuation may be automatically performed via the return spring of trigger (410).

Referring back to FIG. 9, slot (404) includes a detent (406) that impedes the longitudinal actuation of peg (444) until a sufficient force is applied. Thus, detent (406) may prevent inadvertent longitudinal movement of second ratcheting member (440). In addition, or in the alternative, second ratcheting member (440) may be coupled to a spring (448) to bias second ratcheting member (440) proximally. Accordingly, the user may need to overcome one or both of detent (406) and spring (448) to actuate second ratcheting member (440) distally to disengage chevron ratcheting assembly (430). Furthermore, a camming ramp (436) or pin may extend from first ratcheting member (432) to move peg (444) distally once trigger (410) is completely actuated, thereby automatically releasing second ratcheting member (440). Of course chevron ratchet assembly (430) and/or actuator handle assembly (400) may be further configured in accordance with ratcheting assemblies of hemostats, needle holders, mosquito clamps, and/or in any other manner as will be apparent to one of ordinary skill in the art in view of the teachings herein.

III. Exemplary Ratcheting Features with Automatic Releases

While the foregoing examples discussed exemplary ratcheting assemblies to secure trigger (74) during a firing stroke from returning to the unfired position, in some instances, it may be useful to a user to have an automatic release mechanism once the trigger is fully actuated. While the following examples are discussed in reference to other exemplary trigger ratcheting assemblies, it should be understood that the following automatic release assemblies may be incorporated into the ratcheting assemblies discussed previously.

A. Exemplary Rotary Ratchet Assembly with Ramp Release

Figure 11:
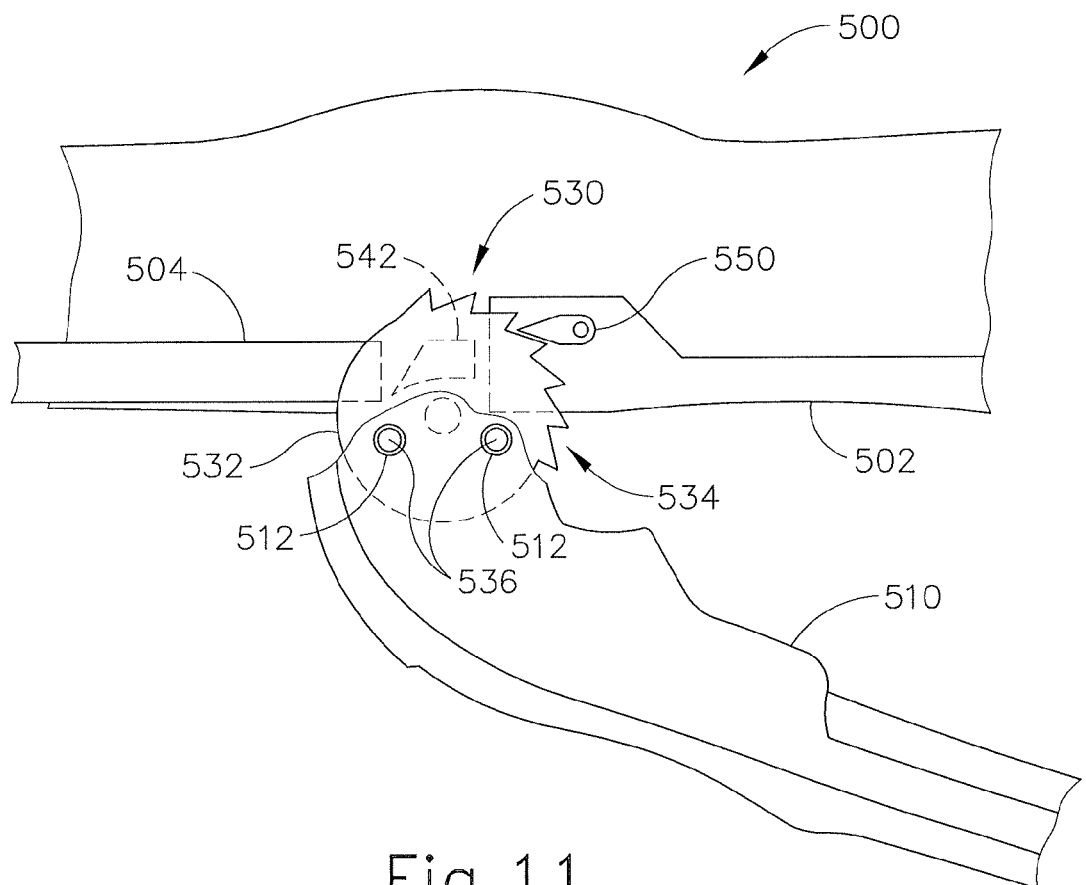
FIG. 11 depicts a partial side elevation view of still another exemplary actuator handle assembly with a portion of the body removed to show an exemplary rotary ratchet assembly with ramp release.
Figure 12:
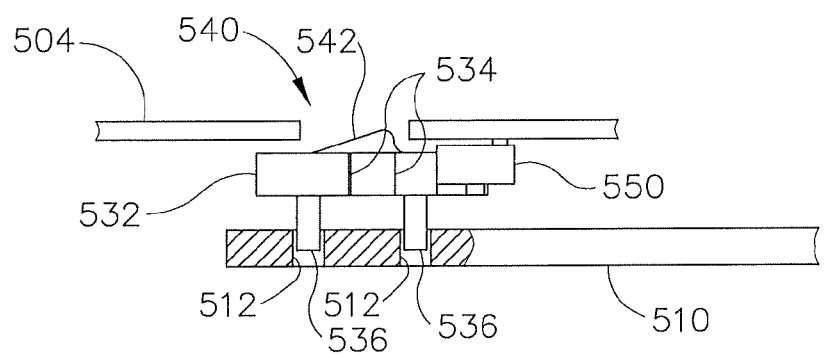
FIG. 12 depicts a partial top elevation view of the rotary ratchet assembly of FIG. 11 showing an exemplary ramp release.

FIGS. 11-12 show yet another actuator handle assembly (500) having a rotary ratchet assembly (530) for surgical stapling instrument (10) described above. In the present example, actuator handle assembly (500) comprises a body (502) and a trigger (510). Body (502), trigger (510), and/or actuator handle assembly (500) may be constructed in accordance with at least some of the teachings of body (72), trigger (74), and/or actuator handle assembly (70) described above. Trigger (510) of the present example is pivotably mounted to body (502) and is coupled to a circular ratcheting member (532) of ratchet assembly (530). In some versions, trigger (510) may include a return spring (not shown) operable to urge trigger (510) back to the unfired position.

As shown in FIG. 11, ratchet assembly (530) comprises circular ratcheting member (532) coupled to trigger (510) and a pawl or idler arm (550). Pawl (550) comprises a toothed member configured to engage one or more teeth (534) of ratcheting member (532) to prevent trigger (510) from actuating back to an unfired position. Pawl (550) may be further configured in accordance with pawls (240, 340) disclosed herein and/or otherwise. In the present example, ratcheting member (532) comprises a plurality of teeth (534) disposed about the circumferential surface of ratcheting member (532). Referring to FIG. 12, ratcheting member (532) is coupled to trigger (510) by a pair of axles (536) that insert into holes (512) formed in trigger (510). Axles (536) and holes (512) are configured such that ratcheting member (532) can actuate laterally relative to trigger (510), yet rotates with trigger (510). In some versions, axles (536) may protrude out of holes (512) and include a flared end (not shown) to prevent ratcheting member (532) from decoupling from trigger (510).

An interior surface (540) of ratcheting member (532) also includes a ramp (542) configured to cam against an interior member (504) of body (502). Ramp (542) of the present example is positioned such that the apex of ramp (542) engages interior member (504) when trigger (510) is fully actuated. Of course, it should be understood that ramp (542) may reach the apex point at other positions of the firing stroke as well. In addition, the height of ramp (542) is sized such that, when the apex of ramp (542) engages interior member (504), ratcheting member (532) is laterally displaced along axles (536) by a sufficient distance to disengage pawl (550). Accordingly, as ratcheting member (532) is rotated via trigger (510), ramp (542) engages interior member (504) and ratcheting member (532) is slidably urged outward on axles (536) toward trigger (510). Once trigger (510) is fully actuated—corresponding to fully firing the instrument—then ratcheting member (532) is fully disengaged from pawl (540) and trigger (510) may be rotated back to the unfired position. In some versions, the user may realign ratcheting member (532) with pawl (540) by pushing ratcheting member (532) inwardly via the protruding axles (536). In other versions, ratcheting member (532) may be biased inwardly via a spring (not shown) and a selectively releasable catch (not shown) may retain ratcheting member (532) against trigger (510) when resetting trigger (510) to the unfired position. Still further constructions for ratchet assembly (530) and/or actuator handle assembly (500) will be apparent to one of ordinary skill in the art in view of the teachings herein.

B. Exemplary Ratcheting Trocar Assembly with Trigger Release

Figure 13A:
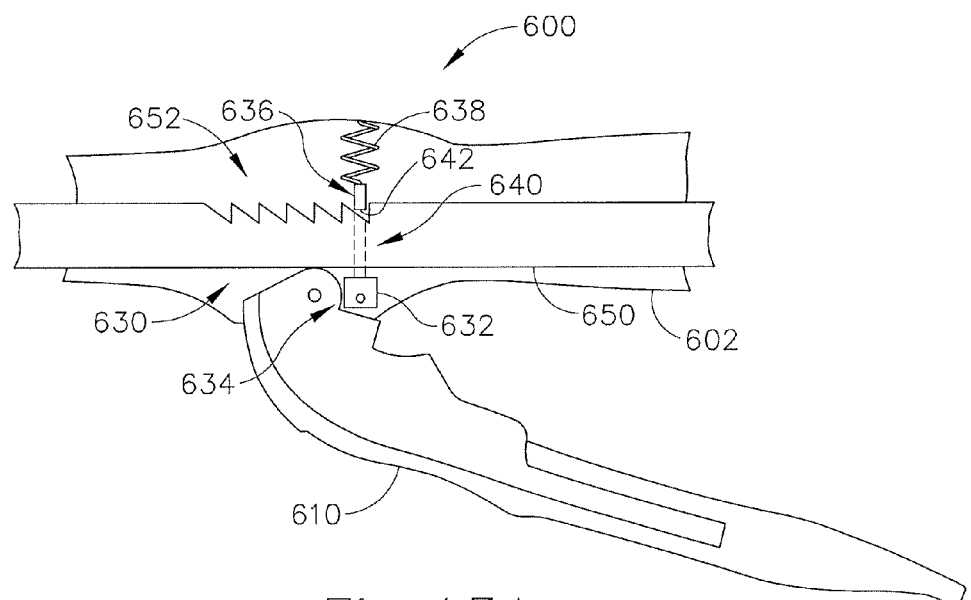
FIG. 13A depicts a partial side elevation view of an exemplary actuator handle assembly with a portion of the body removed to show an exemplary ratcheting trocar assembly.
Figure 13B:
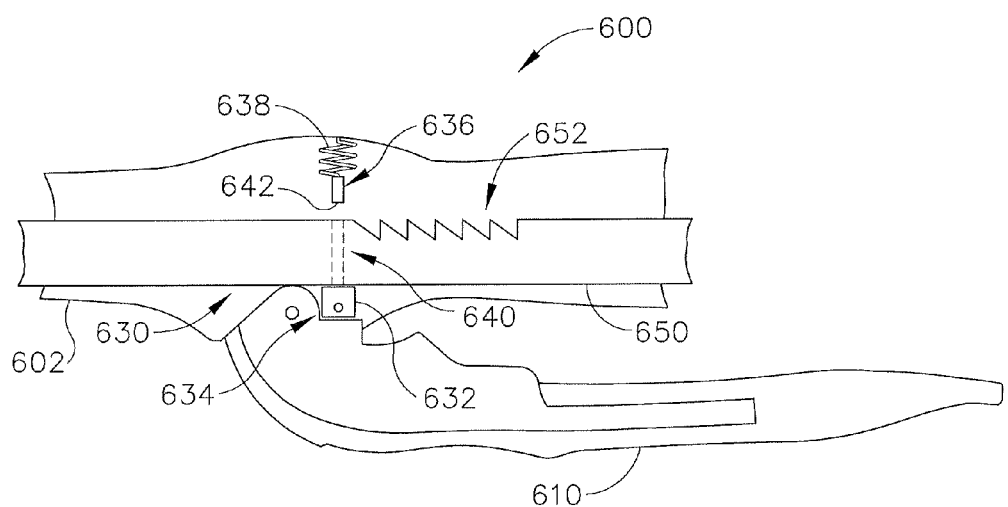
FIG. 13B depicts a partial side elevation view of the ratcheting trocar assembly of FIG. 13A with a trigger engaging a trocar release.

FIGS. 13A-13B depict still another actuator handle assembly (600) having a linear ratchet assembly (630) for surgical stapling instrument (10) described above. In the present example, actuator handle assembly (600) comprises a body (602) and a trigger (610). Body (602), trigger (610), and/or actuator handle assembly (600) may be constructed in accordance with at least some of the teachings of body (72), trigger (74), and/or actuator handle assembly (70) described above. Trigger (610) of the present example is pivotably mounted to body (602) and is coupled to a trocar release (632) of ratchet assembly (630). In some versions, trigger (610) may include a return spring (not shown) operable to urge trigger (610) back to the unfired position.

In the present example shown in FIG. 13A, linear ratchet assembly (630) comprises a ratcheting trocar (650) and a trocar release (632). Trocar (650) extends longitudinally within body (602) and includes a plurality of ratcheting teeth (652) formed on an outer surface of trocar (650). Trocar (650) may be further constructed in accordance with at least some of the teachings of trocar (38) described above. Trocar release (632) is pivotably coupled at a first end (634) to trigger (610) and coupled to a spring (638) at a second end (636). An aperture (640) is formed through trocar release (632) such that trocar (650) extends therethrough. An upper edge (642) of aperture (640) is configured to engage with teeth (652) of trocar (650) such that trocar (650) cannot be actuated distally once upper edge (642) is engaged with teeth (652). Spring (638) biases trocar release (632) downwardly to maintain upper edge (642) in engagement with teeth (652). Accordingly, as trocar (650) is actuated proximally to close the anvil gap, discussed above, linear ratchet assembly (630) prevents trocar (650) from substantially actuating distally. If a user just partially actuates trigger (610) and releases trigger (610), then the anvil gap will be unaffected such that any partially actuated staples should substantially maintain their position until trigger (610) is later fully actuated. If a user needs to reposition trocar (650), a user may manually actuate trocar release (632) to disengage upper edge (642) from teeth (652). By way of example only, a slider, button, etc. may be provided to allow the user to manually actuate trocar release (632) without requiring trigger (610) to be actuated.

Once trocar (650) is positioned in a desired position, trigger (610) is actuated to fire the device. When trigger (610) reaches the fully fired position, trigger (610) actuates trocar release (632) upwardly, as shown in FIG. 13B. This disengages upper edge (642) from teeth (652), thereby permitting trocar (650) to actuate distally to increase the anvil gap. In some versions, a catch or detent (not shown) may engage upper edge (642) to retain trocar release (632) in the position shown in FIG. 13B even if trigger (610) is actuated back to the unfired position. In addition, or in the alternative, teeth (652) may be provided on a driver actuator, such as driver actuator (64) described above, such that ratchet assembly (630) is operable to provide a ratcheting system for firing the device. Of course still other configurations or operabilities for ratchet assembly (630) will be apparent to one of ordinary skill in the art in view of the teachings herein.

C. Exemplary Screen Door Lock Assembly

Figure 14A:
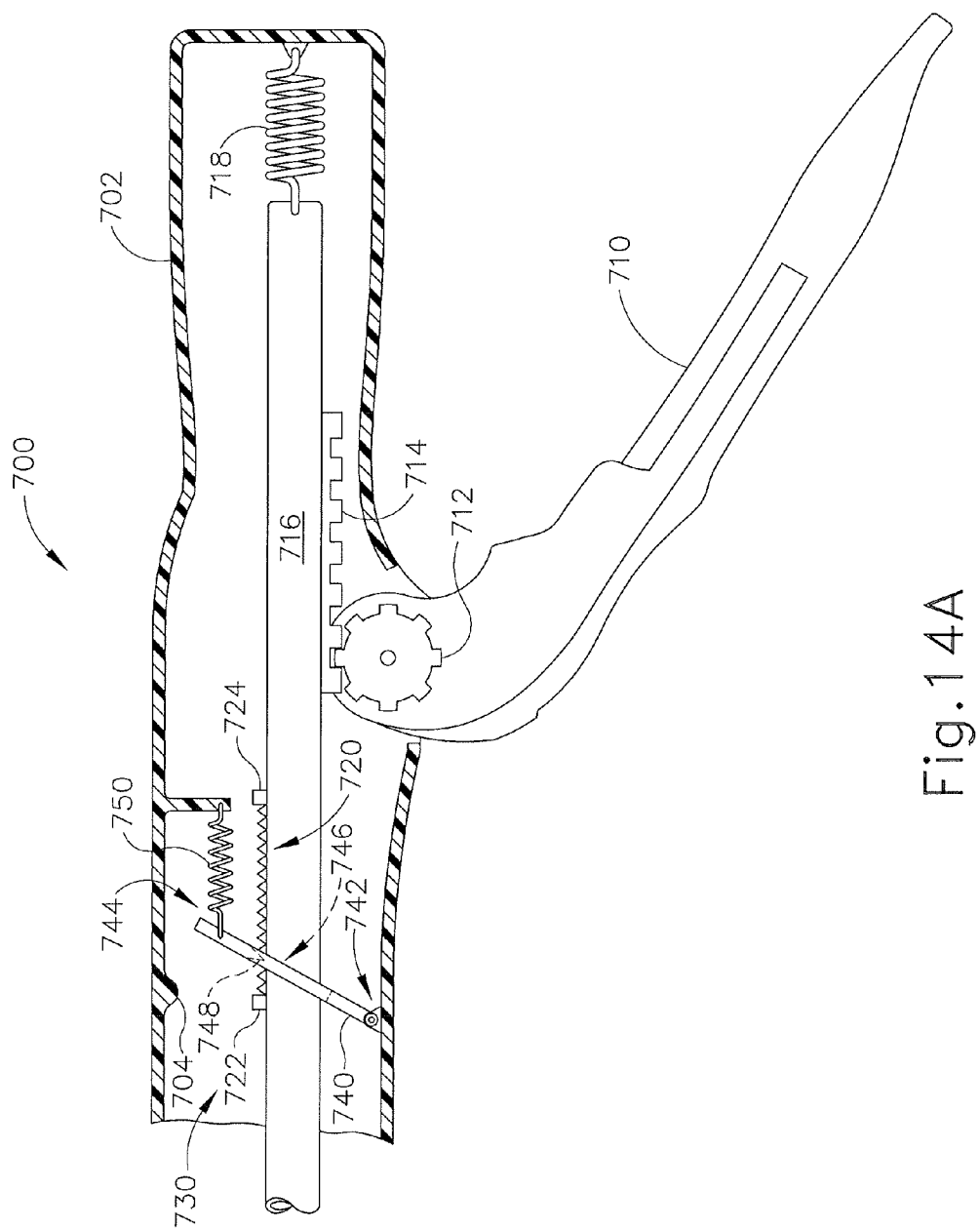
FIG. 14A depicts a schematic view of an exemplary actuator handle assembly showing an exemplary screen door lock assembly.
Figure 14B:
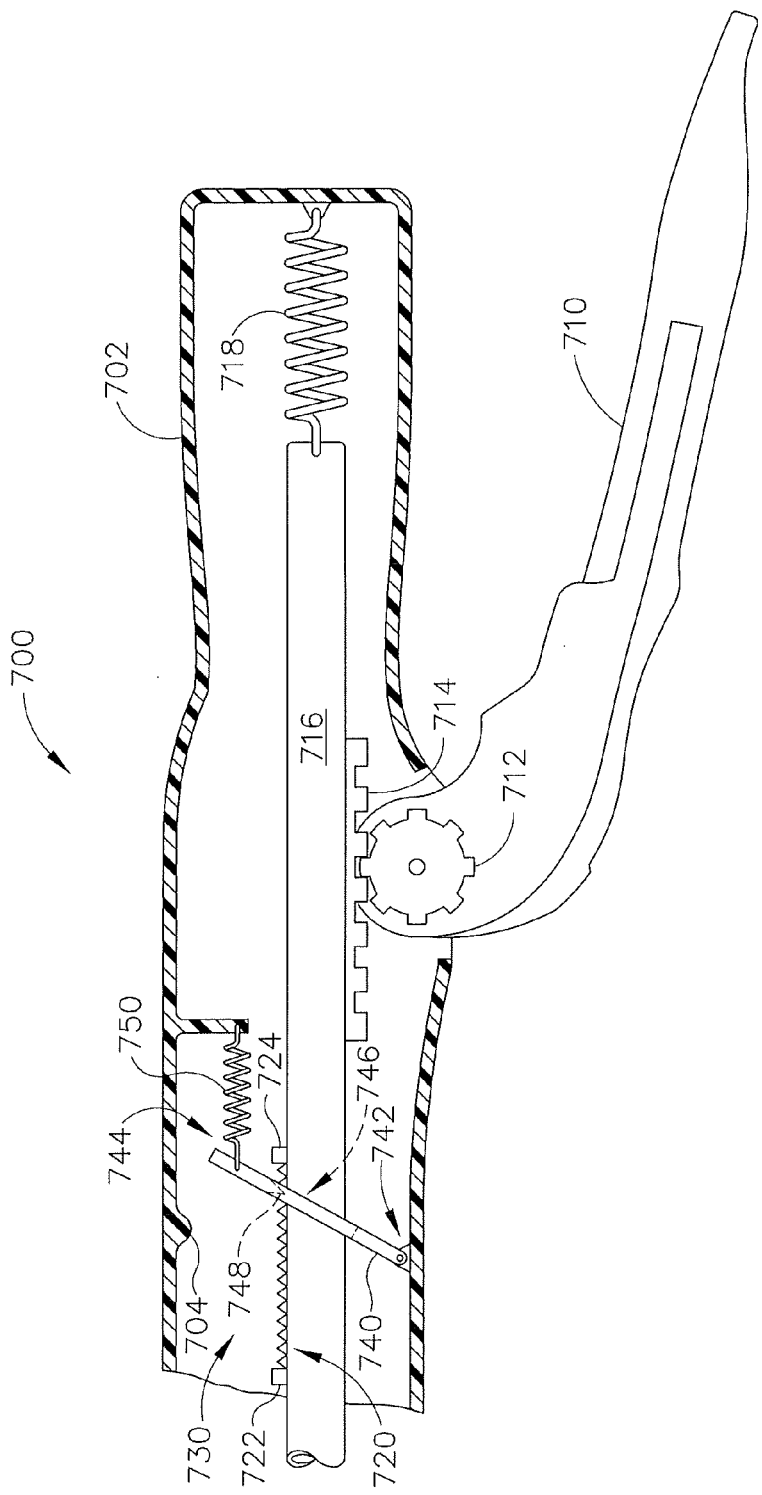
FIG. 14B depicts a schematic view of the screen door lock assembly of FIG. 14A showing the screen door lock member midway through a firing stroke.
Figure 14C:
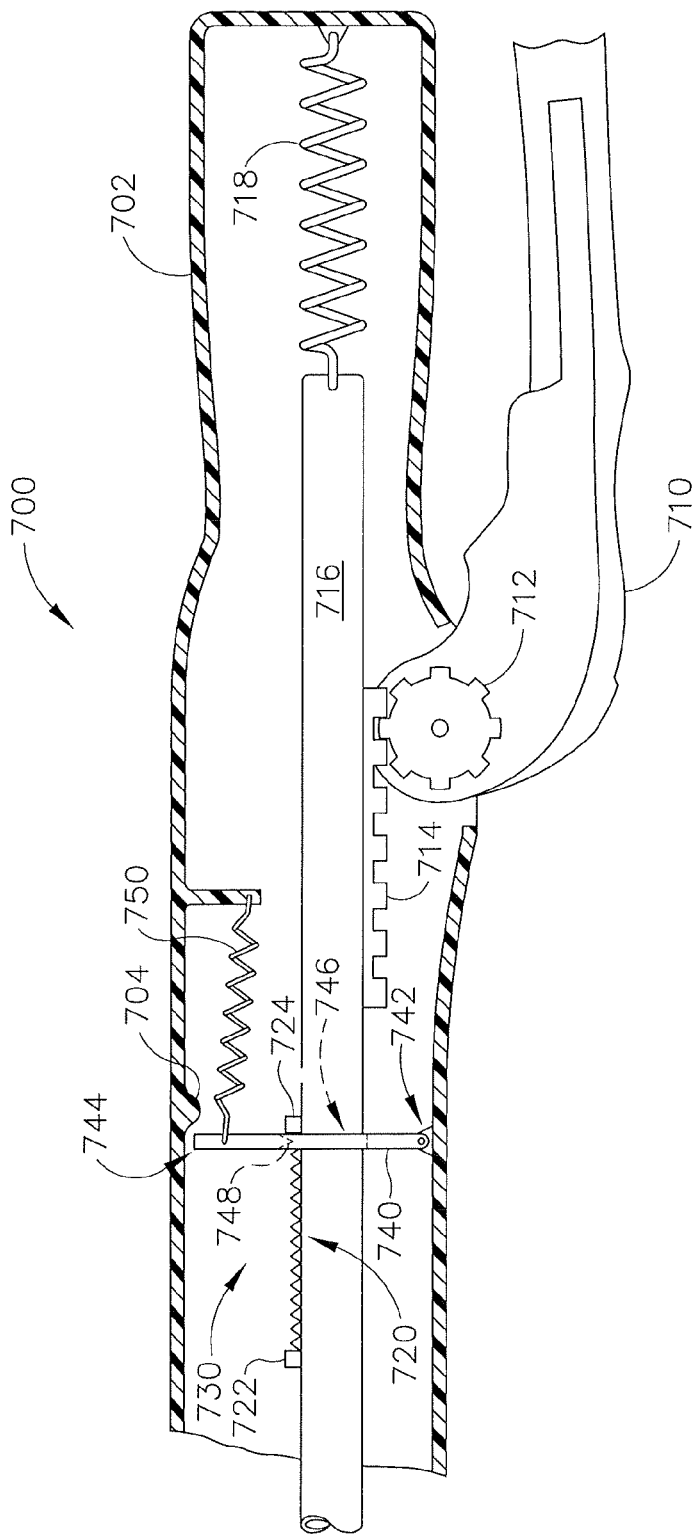
FIG. 14C depicts a schematic view of the screen door lock assembly of FIG. 14A showing the screen door lock member actuated by a firing completion feature to disengage the screen door member.

FIGS. 14A-14C depict an actuator handle assembly (700) having a screen door lock assembly (730) for surgical stapling instrument (10) described above. In the present example, actuator handle assembly (700) comprises a body (702) and a trigger (710). Body (702), trigger (710), and/or actuator handle assembly (700) may be constructed in accordance with at least some of the teachings of body (72), trigger (74), and/or actuator handle assembly (70) described above. Trigger (710) of the present example is pivotably mounted to body (702) and is coupled to a cog (712). In some versions, trigger (710) may include a return spring (not shown) operable to urge trigger (710) back to the unfired position, though this is merely optional.

Referring initially to FIG. 14A, trigger (710) and cog (712) are configured to engage and actuate a rack gear (714) mounted to a driver actuator (716). Driver actuator (716) of the present example may be further constructed in accordance with driver actuator (64) described above. When trigger (710) is in the unfired position, as shown in FIG. 14A, cog (712) is engaged with a distal end of rack gear (714). As trigger (710) is pivoted toward the fired position, shown in FIGS. 14B-14C, cog (712) meshes and actuates rack gear (714) and driver actuator (716) distally. A return spring (718) is coupled to a proximal end of driver actuator (716) to provide a proximal bias that urges driver actuator (716) and trigger (710) toward the unfired position. Of course other actuation components and/or assemblies in view of the teachings herein.

Screen door lock assembly (730) comprises a pivotable screen door washer member (740) that engages an outer surface of driver actuator (716) and serves as a lock. In some instances, screen door washer member (740) may be constructed in a similar manner to the lock provided on a screen door piston, though this is merely optional. In the present example, a row of teeth (720) are disposed on the outer surface of driver actuator (716) to further engage and secure screen door washer member (740) relative to driver actuator (716). Of course, it should be understood that a series of indentations, ribbing, dimpling, and/or otherwise may be included in addition or in the alternative. A firing return feature (722) and a firing completion feature (724), described in greater detail below, are positioned at opposing ends of the row of teeth (720). Screen door washer member (740) is pivotably mounted to body (702) at a first end (742). A second end (744), opposite first end (742), is coupled to a door spring (750) mounted to body (702). Door spring (750) biases screen door washer member (740) proximally relative to body (702). Screen door washer member (740) further includes a central longitudinal aperture (746) (shown in phantom) and a tab (748) (shown in phantom). In the present example, central longitudinal aperture (746) is sized to permit driver actuator (716) to extend through screen door washer member (740) even when screen door washer member (740) is pivoted from a first position, shown in FIG. 14A, to a second position, shown in FIG. 14C. Tab (748) is configured to engage teeth (720) to prevent driver actuator (716) from translating proximally once firing has begun. As shown in the sequence from FIG. 14A-14B, as trigger (710) is pivoted to fire the instrument, tab (748) successively engages teeth (720) as driver actuator (716) is translated distally by cog (712) and rack gear (714).

Referring now to FIG. 14C, firing completion feature (724) is positioned at an end of the row of teeth (720) such that firing completion feature (724) engages screen door washer member (740) when trigger (710) is pivoted to the fully fired position. In the present example, firing completion feature (724) comprises a block that abuts a proximal face of screen door washer member (740) to push screen door washer member (740) distally against the proximal bias provided by door spring (750). As screen door washer member (740) is pivoted to the second position by firing completion feature (724), second end (744) encounters a detent (704). Detent (704) is formed on the interior of body (702) and is positioned to engage and retain screen door washer member (740) in the second position shown in FIG. 14C. Once screen door washer member (740) is pivoted to the second position, tab (748) is disengaged from teeth (720). Accordingly, driver actuator (716) and trigger (710) may be returned to the unfired position after a completed firing via the proximal bias provided by return spring (718).

As driver actuator (716) nears the end of its proximal translation after a completed firing, firing return feature (722) engages a distal face of screen door washer member (740). In the present example, firing return feature (722) comprises a block that abuts the distal face of screen door washer member (740) to push screen door washer member (740) proximally against detent (704). Once second end (744) of screen door washer member (740) clears detent (704), driver actuator (716) and trigger (710) are positioned back to the unfired position shown in FIG. 14A. The instrument may then be removed from the patient. In some versions, a new staple cartridge may be inserted into the device for a subsequent use. Of course still further configurations for screen door lock assembly (730) and/or actuator handle assembly (700) will be apparent to one of ordinary skill in the art in view of the teachings herein.

D. Exemplary Automatic Return Ratchet Assembly

FIGS. 15A-18B depict a further exemplary actuator handle assembly (800) having an automatic return ratchet assembly (830) for surgical stapling instrument (10) described above. In the present example, actuator handle assembly (800) comprises a body (802), a trigger (810) (shown best in FIGS. 15A-15B), a trigger actuation assembly (820), and a driver actuator (840). Body (802), trigger (810), trigger actuation assembly (820), driver actuator (840), and/or actuator handle assembly (800) may be constructed in accordance with at least some of the teachings of body (72), trigger (74), trigger actuation assembly (84), driver actuator (64), and/or actuator handle assembly (70) described above. Trigger (810) of the present example is pivotably mounted to body (802) and is operable to translate trigger actuation assembly (820) relative to body (802).

Figure 15A:
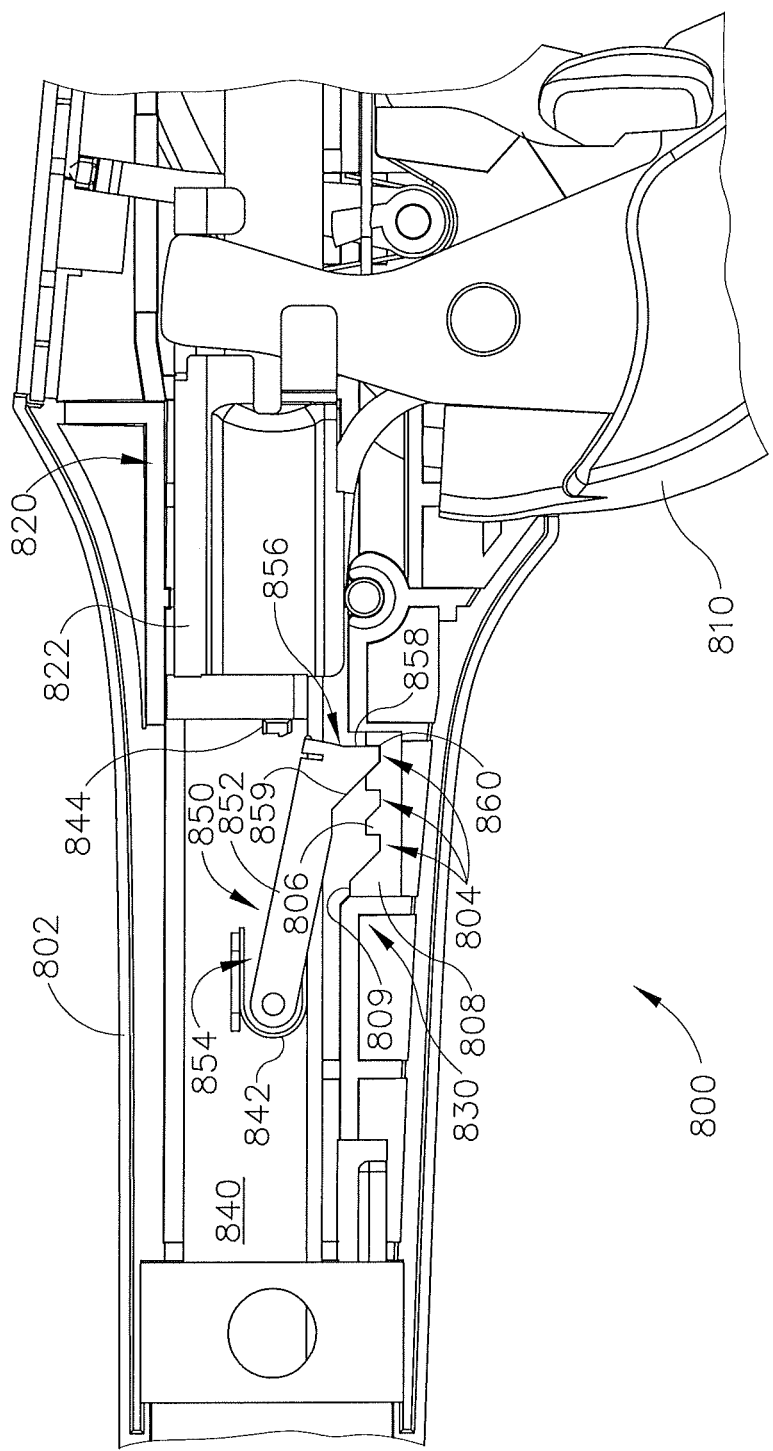
FIG. 15A depicts a partial side elevation view of an exemplary actuator handle assembly with a portion of the body removed to show an exemplary automatic return ratchet assembly having a spring-loaded pawl and ratcheting ramps in an initial position.
Figure 15B:
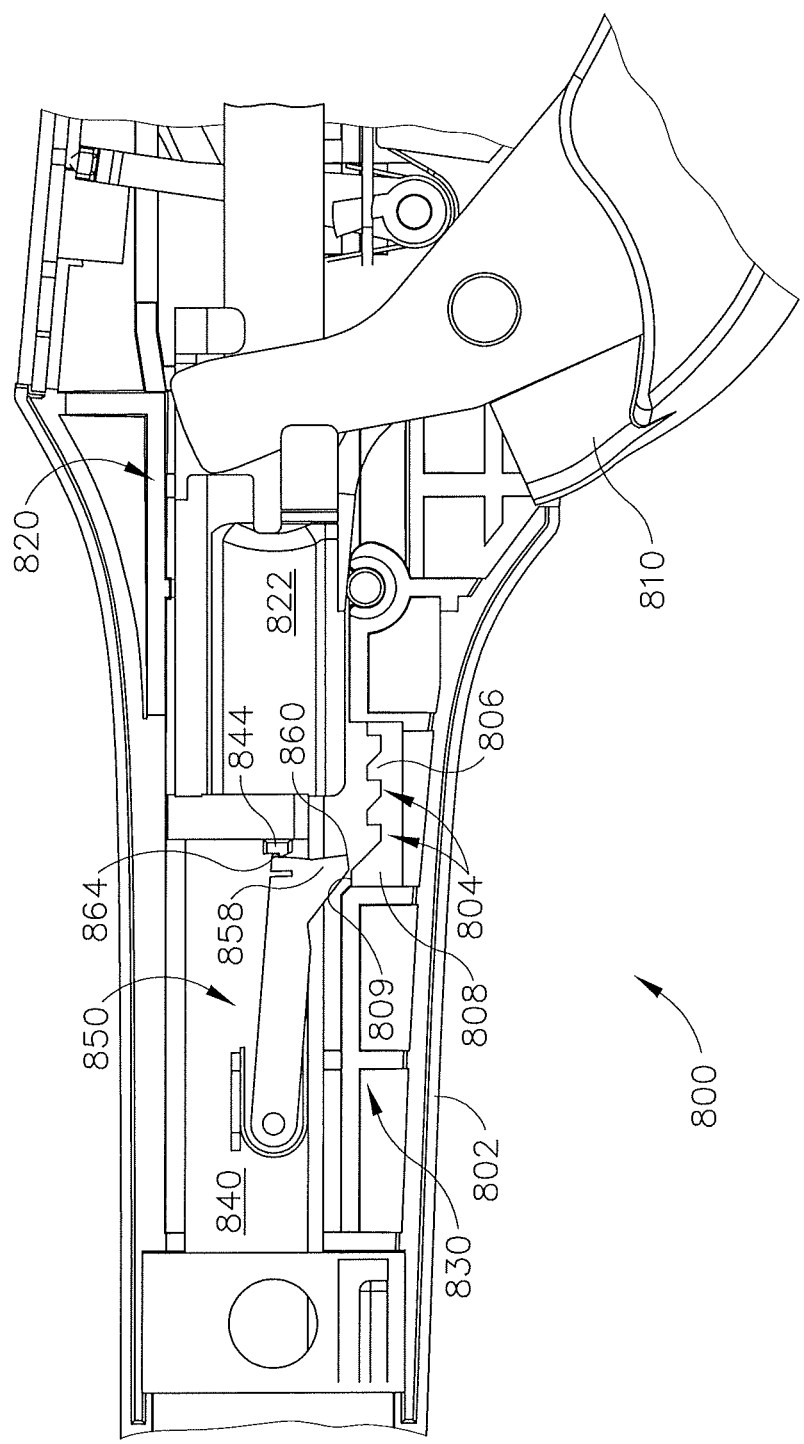
FIG. 15B depicts a partial side elevation view of the automatic return ratchet assembly of FIG. 15A showing the pawl actuated by a final ramp to engage a catch.
Figure 16:
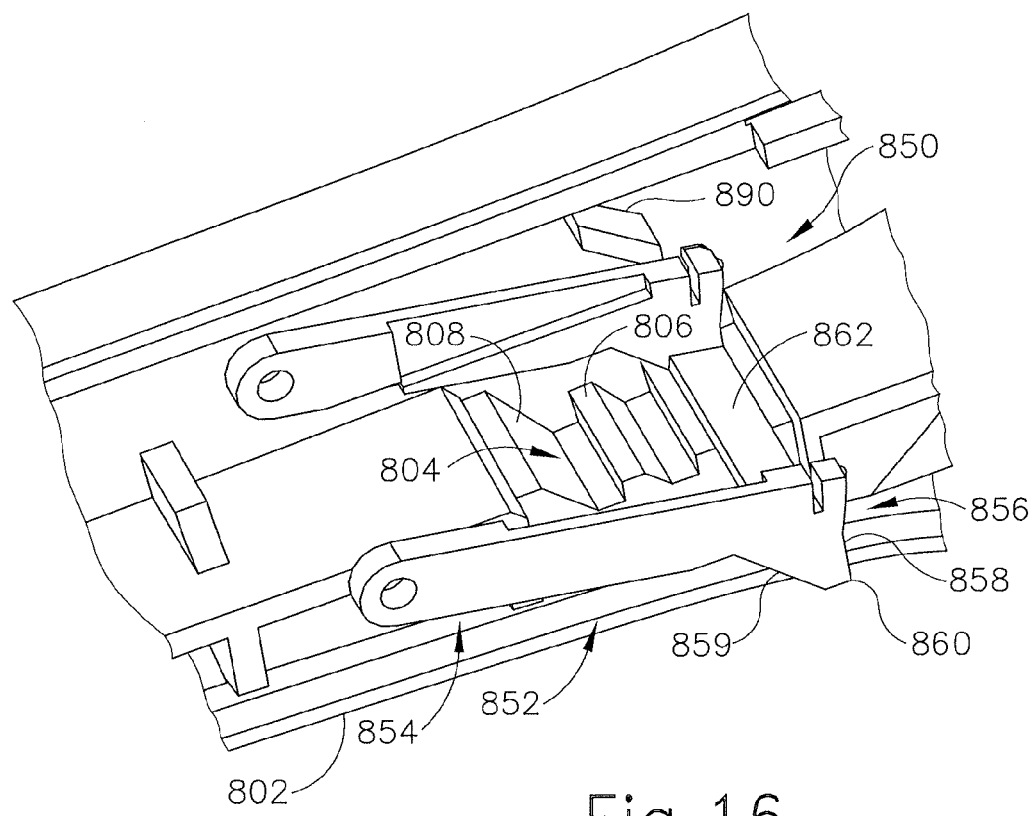
FIG. 16 depicts a partial perspective view of the automatic return ratchet assembly of FIG. 15A with a driver actuator removed.

As shown in FIGS. 15A-15B, trigger (810) is coupled to a trigger actuation assembly (820) to actuate driver actuator (840) distally relative to body (802). Trigger actuation assembly (820) of the present example comprises a slidable trigger carriage (822) engaged with a proximal end of driver actuator (840) such that pivoting of trigger (810) pushes trigger carriage (822) and driver actuator (840) distally. A spring-loaded pawl (850) is pivotably carried by driver actuator (840). A pair of springs (842) are coupled to driver actuator (840) and are operable to bias pawl (850) away from driver actuator (840). Referring briefly to FIG. 16, pawl (850) comprises a pair of arms (852) coupled together by a central member (862). Arms (852) comprise elongate members pivotably mounted to driver actuator (840) at a first end (854). A downward extension (858) protrudes from a second end (856) of each arm (852) and terminates in a locking feature (860). Downward extension (858) includes a distal ramp (859) configured to cam pawl (840) upwardly as distal ramp (859) encounters ramps (806, 808) described below. Of course, it should be understood that distal ramp (859) is merely optional and downward extension (858) may simply be a vertical member. Locking feature (860) is configured to engage notches (804) formed in body (802), as will be described below. Central member (862) spans between arms (852) to form a unitary structure for pawl (850), shown best in FIG. 16. In the present example, central member (862) spans between locking features (860) to form an elongate angled member to engage notches (804). Of course central member (862) may be omitted or may span between arms (852) at other locations. A nodule or detent (864) (shown in greater detail in FIG. 17) is positioned on a proximal end of one or both arms (852) to engage a catch (844) located on driver actuator (840). A tab (866) extends outwardly from the one or both arms (852) and, in the present example, is position adjacent to nodule (864).

Referring back to FIGS. 15A-15B, locking features (860) and/or central member (862) engage notches (804) formed in body (802). In the present example, three notches (804) are formed in body (802), though any number may be used. Notches (804) are longitudinally spaced apart by ramps (806, 808) having flat distal faces and ramped proximal faces. In the present example, two intermediate ramps (806) are positioned proximal of a final ramp (808), though any number of intermediate ramps (806) may be included. Final ramp (808) is configured to terminate at an apex (809) that is higher than the apex of intermediate ramps (806). As will be described in greater detail below, apex (809) and final ramp (808) are sized such that nodule (864) on pawl (850) engages catch (844) of driver actuator (840) when pawl (850) ascends final ramp (808).

Figure 18A:
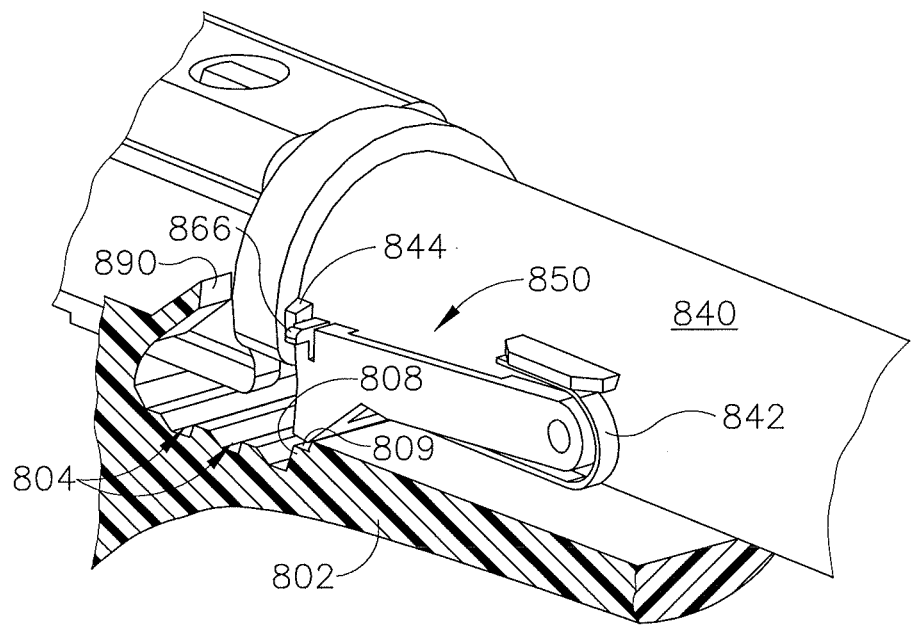
FIG. 18A depicts a partial perspective view of the pawl and catch of FIG. 15B showing a disengagement feature.
Figure 18B:
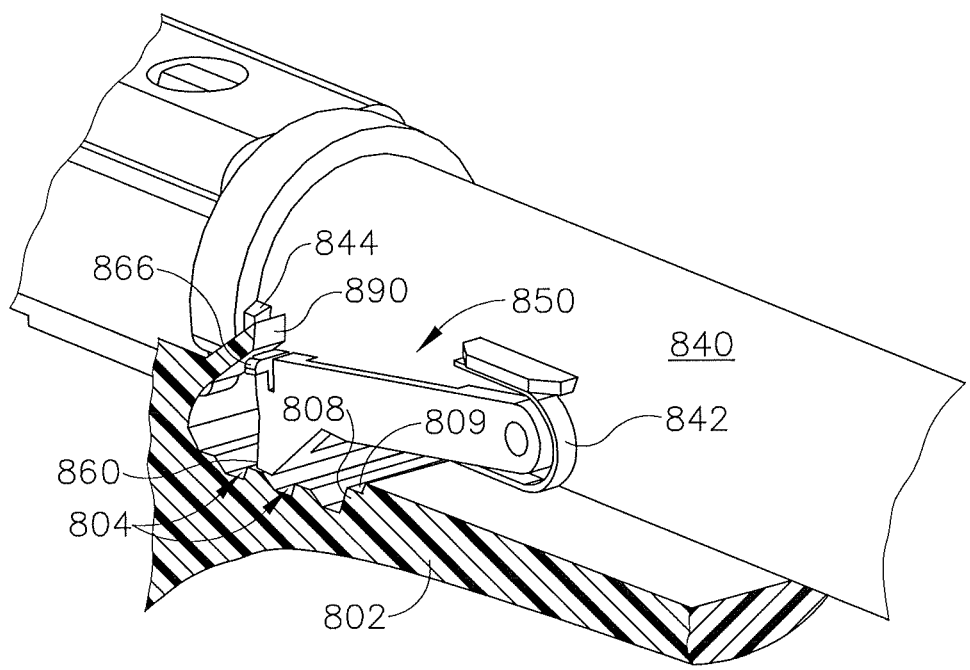
FIG. 18B depicts a partial perspective view of the pawl and disengagement feature of FIG. 18A showing the pawl disengaged from the catch.

Body (802) further includes a disengagement feature (890), shown in FIGS. 16 and 18A-18B, located proximal of final ramp (808) and configured to disengage nodule (864) from catch (844). In the present example, disengagement feature (890) comprises a downwardly sloping ramp that engages tab (866) and urges pawl (850) downward to decouple nodule (864) from catch (844), accordingly, as shown in FIG. 15A, trigger (810), driver actuator (840), and pawl (850) are returned to an initial position. Other disengagement features (890) will be apparent to one of ordinary skill in the art in view of the teachings herein.

When the instrument is not in use, trigger (810), driver actuator (840), and pawl (850) are in the initial position shown in FIG. 15A with locking features (860) and/or central member (862) engaged with a first notch (804). Springs (842) urge pawl (850) toward notches (804) to maintain locking features (860) and/or central member (862) therein. As trigger (810) is actuated, driver actuator (840) is translated distally. Intermediate ramps (806) cam pawl (840) out of notches (804) until locking features (860) and/or central member (862) clear the flat distal face of the corresponding intermediate ramp (806). Once cleared, springs (842) urge pawl (850) into the subsequent notch (804). Accordingly, once pawl (840) has entered the subsequent notch (804), even if a user lets go of trigger (810), driver actuator (840) substantially maintains its position via engagement of locking features (860) and/or central member (862) with notches (804). As driver actuator (840) is translated distally, pawl (850) ratchets into a plurality of notches (804). In some versions, a single intermediate notch (804) may be provided at a predetermined position, such as when the staples begin to protrude from the stapling head assembly. Of course other configurations will be apparent to one or ordinary skill in the art in view of the teachings herein.

Figure 17:
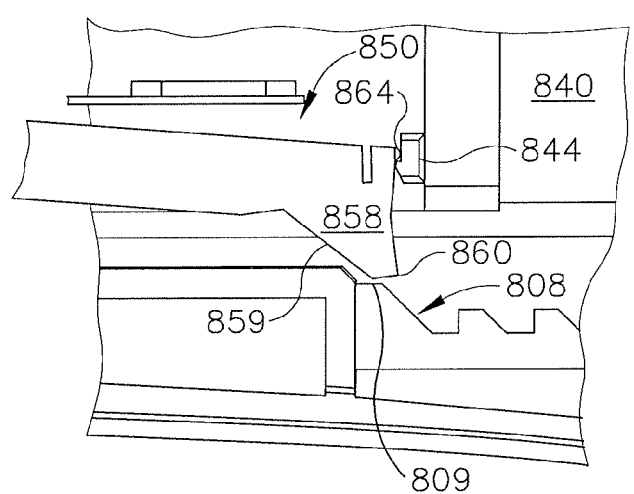
FIG. 17 depicts an enlarged side elevation view of a proximal end of the pawl and the catch of FIG. 15B showing a nodule engaged with the catch.

Referring now to FIGS. 15B and 17, when pawl (850) ascends and reaches apex (809) of final ramp (808), nodule (864) engages catch (844). Final ramp (808) and apex (809) are positioned to correspond to when trigger (810) has been pivoted to the fully fired position. Thus, once the instrument has been fully fired, pawl (850) need not engage notches (804) to prevent proximal translation of driver actuator (840). Accordingly, nodule (864) engages catch (844) to maintain pawl (850) in a position such that locking features (860) and/or central member (862) do not engage notches (804). As shown in FIG. 16, catch (844) may simply comprise a resilient ledge atop of which nodule (864) may rest. Once nodule (864) is engaged with catch (844), a user may manually pivot trigger (810) back to the unfired position and/or a return spring may urge driver actuator (840) and/or trigger (810) back to their initial positions. As shown in FIGS. 18A-18B, as driver actuator (840) and pawl (850) are translated proximally, tab (866) approaches disengagement feature (890). When tab (866) encounters disengagement feature (890), tab (866) (and consequently pawl (850)) are cammed away from driver actuator (840) such that nodule (864) disengages from catch (844). Locking features (860) and/or central member (862) then enter an initial notch (804) to return the device to the initial position, as shown in FIG. 15A.

In some versions, disengagement feature (890) may be located at a different longitudinal position such that disengagement of pawl (850) activates another component. By way of example only, pawl (850) may activate an indicator (mechanically and/or electrically) to indicate to the user that the device has been previously fired or used. In other versions, resetting the instrument may permit a new staple cartridge to be loaded into the device to fire another set of staples into the tissue. In yet a further version, pawl (850) may be pivotably coupled to body (850) and engages notches (804) formed on driver actuator (840), trigger carriage (822), trigger (810), and/or otherwise. Of course still further configurations for automatic return ratchet assembly (830) and/or actuator handle assembly (800) will be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus for stapling tissue, the apparatus comprising:
  (a) a stapling head assembly; and
  (b) an actuator handle assembly comprising:
    i. a body,
    ii. a trigger pivotably mounted to the body, and
    iii. a ratcheting assembly comprising a first member and a second member, wherein the first member is coupled to a drive actuator, wherein the second member is associated with the body, and wherein the trigger is operable to longitudinally actuate the drive actuator relative to the body;
  wherein the trigger is operable to drive one or more staples out of the stapling head assembly; and
  wherein the first member and the second member are configured to engage each other to prevent the trigger from pivoting relative to the body in a first direction, wherein the first member and the second member are configured to engage each other to allow the trigger to pivot relative to the body in a second direction.

2. The apparatus of claim 1 wherein the second member comprises a release feature, wherein the release feature is operable to disengage the second member from the first member.

3. The apparatus of claim 1 wherein the first member comprises a pivotable pawl, wherein the second member comprises a plurality of ramps spaced in such a way to define a plurality of notches, wherein the pawl is operable to engage one or more of the notches when the driver actuator is actuated longitudinally.

4. The apparatus of claim 3 wherein the pawl is resiliently biased towards engagement with the one or more notches.

5. The apparatus of claim 1 further comprising an actuator longitudinally translatable relative to the stapling head assembly, wherein the first member or the second member of the ratcheting assembly is associated with the actuator.

6. An actuator handle assembly for surgical instrument, the assembly comprising:
   (a) a body;
   (b) a trigger pivotably mounted to the body;
   (c) an actuator in communication with the trigger; and
   (d) a ratcheting assembly comprising a first member, a second member, and a third member;
   wherein the first member and the second member are operable to engage each other at a plurality of discrete longitudinal positions relative to the body in order to prevent the actuator from translating in a first direction relative to the body;
   wherein the first member is pivotably coupled to the actuator; wherein the third member is fixed to the actuator, wherein the first member is biased to engage the second member, wherein the third member is operable to selectively engage the first member thereby preventing the first member from engaging the second member; and
   wherein the second member comprises a plurality of ramps formed on the body, wherein the plurality of ramps are spaced in such a way to define a plurality of notches, wherein the first member comprises a pivotable pawl coupled to the actuator, wherein the pawl comprises a locking feature operable to engage one or more notches, wherein the pawl comprises a distal end and proximal end, wherein the distal end is pivotably coupled to the actuator, wherein the locking feature is located on the proximal end.

7. The apparatus of claim 6 wherein the pawl comprises a nodule, wherein the nodule is located on the proximal surface of the locking feature wherein the third member comprises a catch, wherein the catch is configured to selectively secure the pawl via the nodule, wherein the locking feature of the pawl is configured to disengage from the one or more notches when the pawl is selectively secured by the catch.

8. An apparatus for stapling tissue, the apparatus comprising: a stapling head assembly; and an actuator handle assembly comprising: a body, a trigger pivotably mounted to the body, and a ratcheting assembly comprising a first member and a second member; wherein the trigger is operable to drive one or more staples out of the stapling head assembly; and wherein the first member and the second member are configured to engage each other to prevent the trigger from pivoting relative to the body in a first direction, wherein the first member and the second member are configured to engage each other to allow the trigger to pivot relative to the body in a second direction, wherein the second member comprises a release feature, wherein the release feature is operable to disengage the second member from the first member.

* * * * *